United States Patent [19]

Fishman

[11] Patent Number: 5,442,050
[45] Date of Patent: Aug. 15, 1995

[54] **MOLECULAR CLONING OF ANTIGENS SHARED BY RAT- AND HUMAN-DERIVED *PNEUMOCYSTIS CARINII***

[75] Inventor: Jay A. Fishman, Boston, Mass.

[73] Assignee: The General Hospital Corporation, Boston, Mass.

[21] Appl. No.: 781,034

[22] Filed: Oct. 18, 1991

Related U.S. Application Data

[63] Continuation-in-part of Ser. No. 768,166, Sep. 30, 1991, abandoned.

[51] Int. Cl.⁶ .................... C07H 21/04; C12N 15/79
[52] U.S. Cl. .................................. 536/23.7; 435/320.1
[58] Field of Search .................... 536/26, 27, 28, 29, 536/23.7; 435/320.1

[56] References Cited

FOREIGN PATENT DOCUMENTS

| | | | |
|---|---|---|---|
| 0327390 | 8/1989 | European Pat. Off. | 435/6 |
| WO90/13670 | 11/1990 | WIPO | 435/7.1 |
| WO91/02092 | 2/1991 | WIPO | 536/23.7 |

OTHER PUBLICATIONS

Sambrook et al., "Molecular Cloning A Laboratory Manual", 2d ed., Cold Spring Harbor Laboratory Press, 1989, (contents page XXI).
Tanabe, K., et al., Use of *Pneumocystis carinii* Genomic DNA Clones for DNA Hybidization Analysis of Infected Human Lungs, *J. Infectious Diseases* 157(3):593–596 (Mar. 1988).
Wakefield, A. E., et al., "Detection of *Pneumocystis carinii* with DNA Amplification", *The Lancet* 336:451–453 (1990).
Wakefield, A. E., et al., "DNA Amplification on Induced Sputum Samples for Diagnosis of *Pneumocystis carinii* Pneumonia", *The Lancet* 337:1378–1379 (Jun. 8, 1991).
Hayashi, Y., et al., "A Novel Diagnostic Method of *Pneumocystis carinii:* In situ Hybridization of Ribosomal Ribonucleic Acid with Biotinylated Oligonucleotide Probes", *Laboratory Investigation* 63 (4):576–580 (1990).
Graves, D. C., "Immunological Studies of *Pneumocystis carinii*", *J. Protozool.* 36(1):60–69 (Jan.-Feb. 1989).
Fisher, D. J., et al., "Specific T–Cell Response to a *Pneumocystis carinii* Surface Glycoprotein (gp120) after Immunization and Natural Infection", *Infection and Immunity* 59(10):3372–3376 (Oct. 1991).
Gigliotti, F., "Host Species–Specific Antigenic Variation of a Mannosylated Surface Glycoprotein of *Pneumocystis carinii*", *J. Infectious Diseases* 165:329–36 (1992).
Fishman, et al., *Programs and Abstracts of the 31st ICAAC Meeting*, Sep. 29–Oct. 2, 1991, Abstract 227 p. 136 (published Aug. 15, 1991).
Wakefield, A. E., et al., "Cloning of DNA from *Pneumocystis carinii* ", *J. Protozoology* 36(1):5S–7S (1989).
Nakamura, Y., et al., "Structure of Major Surface Determinants and DNA Diagnosis of *Pneumocystis carinii*", *J. Protozoology* 36(1):58S–60S (1989).
Haidaris, C. G., et al., "Molecular Cloning and Characterization of Ferret *Pneumocystis carinii* gp 120", *Program and Abstracts of the 44th Annual Meeting of the Society of Protozoologists*, Jun. 28–Jul. 2, 1991, Abstract WS4, p. 46 (1991).
Nakamura, Y., et al., "Genetic and Immunochemical Study of Major Surface Glycoprotein P115 of *Pneymocystis carinii*", ibid., Abstract WS6, p. 46.

(List continued on next page.)

Primary Examiner—Stephanie W. Zitomer
Attorney, Agent, or Firm—Hamilton, Brook, Smith & Reynolds

[57] ABSTRACT

DNAs encoding antigens of mammalian, *Pneumocystis carinii* including the gp116 major surface antigen of rat and human *P. carinii; P. carinii* DNA containing homologous nucleotide sequences to the antigen encoding DNA; RNAs, proteins, monospecific antibodies and chimeric molecules derived from the DNAs; and probes and diagnostic methods, vaccine compositions and anti-*P. carinii* agents, and methods of treatment for and prophylaxis against *P. carinii* infection and pneumonitis are claimed.

5 Claims, 16 Drawing Sheets

OTHER PUBLICATIONS

Smulian, A. G., et al., "Expression cloning of *Pneumocystis carinii* (Pc) Antigens", ibid., Abstract WS7, p. 47.

Paulsrud, J. R., et al., "Isolation and Characterization of gp120 from *Pneumocystis carinii* from Rat Lung", ibid., Abstract WS2, p. 46.

Linder, E., et al., "Detection of *Pneumocystis carinii* in Lung–Derived Samples Using Monoclonal Antibodies to an 82 kDA Parasite Component", *J. Immunological Methods* 98:57–62 (1987).

Matsumoto, Y., et al., "Production of a Monoclonal Antibody With Specificity for the Pellicle of *Pneumocystis carinii* by Hybridoma", *Parasitology Research* 73:228–233 (1987).

Kovacs, J. A., et al., "Diagnosis of *Pneumocystis carinii* Pneumonia: Improved Detection in Sputum with Use of Monoclonal Antibodies", *N.E. J. Medicine* 318(10):589–593 (1988).

Gigliotti, F. and Hughes, W. T., "Passive Immunoprophylaxis with Specific Monoclonal Antibody confers Partial Protection against *Pneumocystis carinii* Pneumonitis in Animal Models", *J. Clin. Invest.* 81:1666–1668 (1988).

Pottratz, S. T., et al., "*Pneumocystis carinii* Membrane Glycoprotein gp120 is a Fibronectin Binding Protein Which Mediates Pneumocystis Attachment", *Clinical Research* 38(2):466A (1990).

Pottratz, S. T., et al., "*Pneumocystis carinii* Membrane Glycoprotein gp120 Mediates Attachment of Pneumocystis to Host Cells", *Am. Rev. Resp. Dis.* 141:A271 (1990).

Bogucki, M. S., et al., "Characterization of *Pneumocystis carinii* Monoclonal Antibodies", *J. Protozool.* 36(1):41S–43S (1989).

Maddison, S. E., et al., "Detection of Specific Antibody by Enzyme–Linked Immunosorbent Assay and Antigenemia by Counterimmunoelectrophoresis in Humans Infected with *Pneumocystis carinii*", *J. Clinical Microbiol.* 15(6):1036–1043 (1982).

Kovacs, J. A., et al., "Identification of Antigens and Antibodies Specific for *Pneumocystis carinii*", *J. Immunology* 140(6):2023–2031 (1988).

```
      CTCTTATTAAATTTAATTTATTTATTTGCGGTGTTGGTGATACACTATTCTGTACAATCG
  1   ------+---------+---------+---------+---------+---------+    60

GAGATGATTGAATATGTCCTTGTGATGTTTGGTTAGCAGATGAAGATTGCAGTATATTTT
 61   ------+---------+---------+---------+---------+---------+   120

GTGATGTCTGTATTTGTTGTTGCTGCGATTGCTGTTGTGATTGTTGTTGGTGTGGTTGTG
121   ------+---------+---------+---------+---------+---------+   180

ATGATTGTTGGGATTGCTGCTGGGATTGTGGTATTTGATTTTGTGGTGAATGTTGGTTTA
181   ------+---------+---------+---------+---------+---------+   240

AATGCCCTTGTGTATGATTTATATTTTGCATTTGAATATTACGGTTTTGATTTTGATTAA
241   ------+---------+---------+---------+---------+---------+   300

CTAAATGCTGCATTATTTGCTGCTGCTGCCATATTGTACTGGGTTGATTTGTTCGTACTA
301   ------+---------+---------+---------+---------+---------+   360

CTCTTGGATTTATTAAATGTTCTGGCCTACCATTTATCATAGCCATCTGCATTTGCGGAT
361   ------+---------+---------+---------+---------+---------+   420

TATTCACATAAATGGATTGATCAGTCATTTGAGATCTCATAATATGTCCATTATGACCCA
421   ------+---------+---------+---------+---------+---------+   480

TCATTATTCCATCGTTTTGCATATCTCCCATAGTTTTGCTTGATTGAAAAACATAATTT
481   ------+---------+---------+---------+---------+---------+   540

GTGGATGAGTGTCGGATTGAATTTGGCCATTGTATCCTGCAATACTAGGTGAAGTATTTC
541   ------+---------+---------+---------+---------+---------+   600

TTGAAGTATTATTTTGTTGAGAAAGTGGACCATCGGTAGGTGAATTAGGGGAATTTTGAT
601   ------+---------+---------+---------+---------+---------+   660

GAGCCACTTTTGAAATGCCGCGTTTAGTATCATTATGATTATTTTCGGAGAAAGAGCAT
661   ------+---------+---------+---------+---------+---------+   720

TTCTAACTCCTTGTGGAGATAAAATCTGAAAAGTGGATGAATCTTGTGATTGAAGTCGTT
721   ------+---------+---------+---------+---------+---------+   780

CTTGATCTTGATGTGTCATCATAAGGCGTTTTTTATTCTGCTGTTCAAGAAACATAAGCT
781   ------+---------+---------+---------+---------+---------+   840

GCATTTGATAATCTTCAAGAGTATGATTATTAGGATTTGTCGGGCAGTTTTGCTGAGACG
841   ------+---------+---------+---------+---------+---------+   900

GTAATATATTTCCATAAAAATCATTAGGCCCCATTTCATTTCCATCACCCGTCATTATTG
901   ------+---------+---------+---------+---------+---------+   960
```

FIG. 5A

```
961   ATGAAGGAAGACATTGATTTGAAATTTGCCCTTTAGGAATATTTAGAACTCTTTGTTGTT   1020

1021  GATTCGAAAAACCCTGTGTATATTTTTGCAATTGTCTCTGTTGCATAGAGGGCGTTTGTG   1080

1081  ATTGAAATGCAGTAAATTGCTGTTGTGTAAGACCGACCGGGTTAATTCCGGTTAAGAGGC   1140

1141  AAGCACAAGTAGTACAAGTAGCACAAGATGAGATTAAGGAGGAACACCTTTTGGCTTTCA   1200

1201  TTGTGAAGGACAAACATGATGATGAGAATGAATGCAAAAAAAGGCTCGAGGAATATTGTA   1260

1261  AAGAGTTGAAGAAAGCAGATGAGAATTTCAGTGTGAATGAGAAAGTTAAAGGACTTTGTG   1320

1321  ATGATAAAAAACGAGACGAAAAATGCAAAGAACTGAAAAAAAAAGTTAAAGATGAATTGG   1380

1381  GAACTTTTGATACGGATCTTGAAGCATCGGTAGATGACATAGAAGATGAAGGAGTTTGTA   1440

1441  AAAAACATGAAGAAAAATGTATACTTTTAGAGGAAGCAGACCCAAATAGTCTTAAGGAGA   1500

1501  ACTGTGTCAAGTTGAGGGAAGGATGTTACGAATTGAAGCGTAAAAAGGTGGCAGAGGAGC   1560

1561  TCCTTTTGAGGGCGCTCGGAGGGGATGCTAAAGATGAAGCTAAATGTAAAGAAAAGATGA   1620
                                                                M  K

1621  AAACTGTTTGCCCAATGTTAAGCCGAGAAAGTGACGAGCTGATGTTTTTCTGCCTTGATT   1680
       T  V  C  P  M  L  S  R  E  S  D  E  L  M  F  F  C  L  D  S

1681  CGGATGGAACGTGTAAAGCGCTGAAAACAAAATCAGAAGAAGTTTGCCTGCCTTTAAAAG   1740
       D  G  T  C  K  A  L  K  T  K  S  E  E  V  C  L  P  L  K  E

1741  AAAAGCTTAAAGATGGCGAATTAAAGGAAAAATGTCATGAAAGACTTGAGAAATGTCATT   1800
       K  L  K  D  G  E  L  K  E  K  C  H  E  R  L  E  K  C  H  F
```

FIG. 5B

```
      TTTACAAAGAAGCGTGTACTGAAACAAAGTGTGATGAGGATATGAAGCAATGCAAGGAAA
1801  ------------+---------+---------+---------+---------+---------+  1860
       Y  K  E  A  C  T  E  T  K  C  D  E  D  M  K  Q  C  K  E  K

AAGGATTCACATATAAAGCGCCGGAATCTGATTTTAGTCCTGTCAAGCCGAAGGCGTCGT
1861  ------------+---------+---------+---------+---------+---------+  1920
        G  F  T  Y  K  A  P  E  S  D  F  S  P  V  K  P  K  A  S  L

TGTTGAGAAGTATTGGGTTGGATGATGTGTATAAAAAGGCTGAAAAAGAAGGAATTATTA
1921  ------------+---------+---------+---------+---------+---------+  1980
       L  R  S  I  G  L  D  D  V  Y  K  K  A  E  K  E  G  I  I  I

TTGGAAAATCAGGAGTGGATCTACCAAGGAAGTCAGGTACAAAATTTCTGCAAGATCTCT
1981  ------------+---------+---------+---------+---------+---------+  2040
        G  K  S  G  V  D  L  P  R  K  S  G  T  K  F  L  Q  D  L  L

TGCTACTGTTGAGCAGAGATGAGAATGATGCAGGGAAGAAATGCGGTAAAGCGTTAGGAA
2041  ------------+---------+---------+---------+---------+---------+  2100
        L  L  L  S  R  D  E  N  D  A  G  K  K  C  G  K  A  L  G  K

AATGTGAAACTTCTAAGTATTTGAATACTGATTTGATGGAGTTATGCAAAGATGCTGATA
2101  ------------+---------+---------+---------+---------+---------+  2160
        C  E  T  S  K  Y  L  N  T  D  L  M  E  L  C  K  D  A  D  K

AAGAAAATAAATGCAAAAAAAAGCTAGATGTAAAAGAAAGATGTACAAAACTCAAGTTAA
2161  ------------+---------+---------+---------+---------+---------+  2220
        E  N  K  C  K  K  K  L  D  V  K  E  R  C  T  K  L  K  L  N

ATCTTTATGTGAAAGGGTTGTCTACGGAGTTTAAAGAAGATAAAAAATCACATCTTTTAT
2221  ------------+---------+---------+---------+---------+---------+  2280
       L  Y  V  K  G  L  S  T  E  F  K  E  D  K  K  S  H  L  L  S

CGTGGGGACAGCTTCCAACATTATTTACGAAGGGAGAGTGTGCAGAACTTGAGTCGGAAT
2281  ------------+---------+---------+---------+---------+---------+  2340
        W  G  Q  L  P  T  L  F  T  K  G  E  C  A  E  L  E  S  E  C

GTTTCTATTTAGAAAATGCGTGTAAAGATAATGAGATTGGTGAAGCGTGTCAAAATCTAC
2341  ------------+---------+---------+---------+---------+---------+  2400
        F  Y  L  E  N  A  C  K  D  N  E  I  G  E  A  C  Q  N  L  R

GATCAGCGTGCTATAAAAAGGGACAAGACAGGATGTTGAATAAGTTCTTTCAAAAGGAAT
2401  ------------+---------+---------+---------+---------+---------+  2460
       S  A  C  Y  K  K  G  Q  D  R  M  L  N  K  F  F  Q  K  E  L

TGAAGGGAAAGCTTGGTCATGTAAGATTTTATAGCGATCCTAAAGATTGTAAAAAATATG
2461  ------------+---------+---------+---------+---------+---------+  2520
        K  G  K  L  G  H  V  R  F  Y  S  D  P  K  D  C  K  K  Y  V
```

FIG. 5C

```
      TGGTAGAAAACTGTACAAAACTTAAAAAAGATAAAAGATACCTTTCAAAATGTCTTTATC
2521  ------------+---------+---------+---------+---------+---------+  2580
        V  E  N  C  T  K  L  K  K  D  K  R  Y  L  S  K  C  L  Y  P

CTAAAGAACTATGTTATGGGCTTTCAAATGATATTTTTCTCCAATCCAAAGAGTTAAGTT
2581  ---------+---------+---------+---------+---------+---------+  2640
        K  E  L  C  Y  G  L  S  N  D  I  F  L  Q  S  K  E  L  S  S

CGCTTTTAGATGATCAGAGAGATTTTCCATTTGAAAAGGATTGTCTTGAATTGGGAGAGA
2641  ---------+---------+---------+---------+---------+---------+  2700
        L  L  D  D  Q  R  D  F  P  F  E  K  D  C  L  E  L  G  E  K

AGTGTGATCAACTTAGTAGTGATTCATTATTGAATTTAGAAAAGTGTATAACATTGAAAA
2701  ---------+---------+---------+---------+---------+---------+  2760
        C  D  Q  L  S  S  D  S  L  L  N  L  E  K  C  I  T  L  K  R

GACGCTGTGAATATTTTGACGTTACAGAAAGATTTAGAAAAGTATTTTTAAAAA
2761  ---------+---------+---------+---------+---------+----  2814
        R  C  E  Y  F  D  V  T  E  R  F  R  K  V  F  L  K
```

FIG. 5D

FIG. 6A
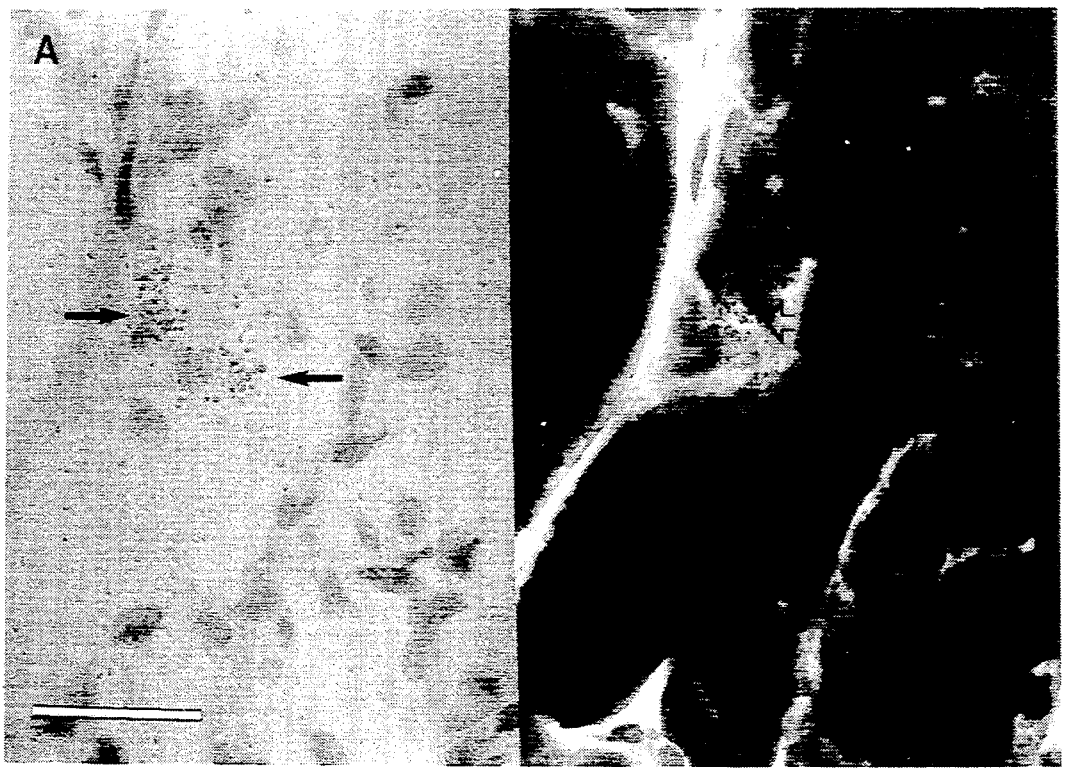
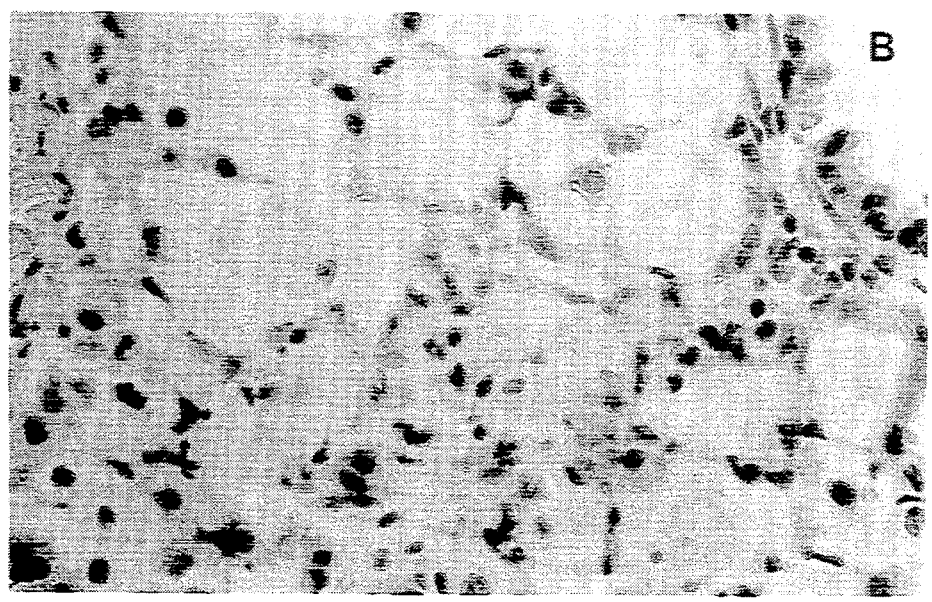
FIG. 6B

```
   1  GTCGACTCTA GAGGATCCCC GGGTACCGAG CTCGAATTCC TTTTTGCGCA
  51  ACTTAGTTGT ATTTTAGTTT ATTCAATAGC AGAAAGGGAT TTCATGTCAT
 101  TAGATGAAAT ATATGAAGGA GGCGATATAA GTTTTGATCA TGAAAAACTC
 151  GAATTTAACG AATATATCAA GTTTTACAAA TGCTTGAAAA GGCAAAAAAT
 201  ATTGGGAACC GGCTTTGTTG ATAGAACCAA AGATTTTTCT AATAGACGAT
 251  ATGAAGGGAG AATTGAGTTA AATCATTTGG GGAGACGCCC AGGAGTCGAC
 301  TATTTTAGGA AAGGTGGGGA TGTTTTTACT GATGGTTATC CTCGTGGAGG
 351  TCATTTGATC GAGGATGAGT TGTCCGAAGA GGCGGCAATG GCACGGCCGG
 401  TTAAGAGGCA AGCACAAGTA GTACAAGTAA GCACAAGATG AGATTAAGGA
 451  GGAACACCTT TTGGCTTTCA TTGTGAAGGA CAAACATGAT GATGAGAATG
 501  AATGCAAAAA AAGGCTCGAG GAATATTGTA AAGAGTTGAA GAAAGCAGAT
 551  GAGAATTTCA GTGTGAATGA GAAAGTTAAA GGACTTTGTG ATGATAAAAA
 601  ACGAGACGAA AAATGCAAAG AACTGAAAAA AAAAGTTGGG GATGAATTGG
 651  GAACTTTTGA TACGGATCTT GAAGCATCGG TAGATGACAT AGAAGATGAA
 701  GGAGTTTGTA AAAAACATGA AGAAAAATGT ATACTTTTAG AGGAAGCAGA
 751  CCCAAATAGT CTTAAGGAGA ACTGTGTCAA GTTGAGGGAA GGATGTTACG
 801  AATTGAAGCG TAAAAAGGTG GCAGAGGAGC TCCTTTTGAG GGCGCTCGGA
 851  AAGGAAGCTA AGAAGAAGT TAAATGTAAA GCAGAGATGA AAAAGGTTTG
 901  CCCAGTGTTA AGCCGAGAAA GCGACGAATT GATGTTTTTG TGCCTTGATT
 951  CGGATGGAAC GTGTCAGCGC TGAAAAAAAA ATCAGAAGAA GTTTGCCAGC
1001  TTTTAAAGAA AGCTTAAAGA TGGCGAATTA AAGGAAAAAT GTCATGAAAG
1051  ACTTGAGAAA TGTCATTTTT ACGGAGAAGC GTGTGATAAA ACAAAATGTG
1101  ATGAGGATAA GGATCAATGC GAGAAAAAAG AAATCACATA TAAGCGCCAG
1151  AATCTGATTC TAGTCCTGTC AAGCCGAAGA CGTCGTTGTT GAGAAGTATT
1201  GGGTTGGATG ATGTGTATAA AGAGCTGAA AAAGAAGGAA TTATTATTGG
1251  AAAATCAGGA GTGGATCTAC CAAGGAAGTC AGGTACAAAA TTTCTGCAAG
1301  ATCTCTTGCT AGTCTTGAGC AGAGATGAGA ATGATAAGGA TGCAGGGAAG
1351  AAATGCGAAA AAGCGTTAAA AAAATGTGAA ACTTCTAGTA TTTGAATACT
1401  GATTTGATGG AGTTATGCAA AGATGCTGAT AAACAAAAAA AGGAATTC
```

FIG. 8

```
                          M
       E T                a         M
       c s                e         a
       o p                I         e
       R E                I         I
       I I                I         I
     GAATTCCTTTTTTTTTTCATAATGGGTTTTTTATTTGTTACGTTTTTATTTTCTATAATA
   1 ----------+---------+---------+---------+---------+---------+ 60
     CTTAAGGAAAAAAAAAAGTATTACCCAAAAAATAAACAATGCAAAAATAAAAGATATTAT

C
       C                 T             C             T      fCH
       Av M              s             Av            s  H   rvp
       li s              p             li            p  p   lia
       uJ e              E             uJ            E  h   OJI
       II I              I             II            I  I   III
       /                                /                   //
     GCTTTAATAAATGCTATTGAAATTTTGTATCCTAAAGCTGGTGATAAATTGCAAGCCGGT
  61 ----------+---------+---------+---------+---------+---------+ 120
     CGAAATTATTTACGATAACTTTAAAACATAGGATTTCGACCACTATTTAACGTTCGGCCA N
               l
               a       M                                      M
               I       s                                      s
               I       e                                      e
               I       I                                      I
     TTACATGAAGTTAAATGGACTACTGAAAGTGCCACTTCTATAGATAAGGTTAATGTGTTT
 121 ----------+---------+---------+---------+---------+---------+ 180
     AATGTACTTCAATTTACCTGATGACTTTCACGGTGAAGATATCTATTCCAATTACACAAA E                      F   N M
                        H c                    C  n  CsP a
       M                l o                    AvMN u Avpv e    B
       s                n 5                    liah 4 liBu I    b
       e                f 7                    uJee H uJII I    v
       I                I I                    IIII I IIII I    I
                                                /// ///
     CTTTTTAATGACAAGGAATCCCCCCCTTTTTACCTTCAGCTAGCAGGTGATGTTACTTTT
 181 ----------+---------+---------+---------+---------+---------+ 240
     GAAAAATTACTGTTCCTTAGGGGGGGAAAAATGGAAGTCGATCGTCGACTACAATGAAAA
                                              E       S
                                              cSBSAa
```

FIG. 9A

```
                                              osscvu
                                              Rotra9
                                              IINFI6
                                              IIIIII
                                              / / /
          TCTAATGGAAAAGTTAGCGTTCCTATACCTTATAATGTCGTTCCTGGTCCTGATTATACT
241      ----------+---------+---------+---------+---------+---------+ 300
          AGATTACCTTTTCAATCGCAAGGATATGGAATATTACAGCAAGGACCAGGACTAATATGA N                     SM
                              d                     pa
                              e                     ee
                              I                     II
          ATTTTACTTACTGCGAAAAATCGATATGATGTTTACGCTACTAGTGGTTCTTTTAGTATT
301      ----------+---------+---------+---------+---------+---------+ 360
          TAAAATGAATGACGCTTTTTAGGTATACTACAAATGCGATGATCACCAAGAAAATCATAA H         C                T                    M
              i         P         v     HM     s      MF      b
              n         l         i     gs     p      so      o
              f         e         J     ae     E      ek      I
              I         I         I     II     I      II      I
          GCAGAGTCTAAACTTTCAGCCGACGCTTGTGTTAATTTTCTTAATGAAGATGGTTCATCC
361      ----------+---------+---------+---------+---------+---------+ 420
          CGTCTCAGATTTGAAAGTCGGCTGCGAACACAATTAAAAGAATTACTTCTACCAAGTAGG S            E                          S
              Aa           Cc BSS              C      a
              vu           voRscs       M      v      u DH
              a9           iRstro       s      i      3 pp
              I6           QIaNFI       e      J      A nh
              II           IIIIII       I      I      I II
              /            / //                       /
          ACTATTGGTCCTGTACCTGGTAAAGTTAAGCCTGTTTCTACTGATCTTGTATCACCTCTG
421      ----------+---------+---------+---------+---------+---------+ 480
          TGATAACCAGGACATGGACCATTTCAATTCGGACAAAGATGACTAGAACATAGTGGAGAC M T
                    B             B   M a s    M
              M     s       M     b   b e p    b       M
              n     p       n     v   o 1 4    o       n
              l     M       l     I   I 1 5    I       l
              I     I       I     I   I I I    I       I
          CCACCTGCACCTCCTGATGAAGACTTTGAAGATTGTGACGAATGTGATGAATGTGAGGAA
481      ----------+---------+---------+---------+---------+---------+ 540
          GGTGGACGTGGAGGACTACTTCTGAAACTTCTAACACTGCTTACACTACTTACACTCCTT C                C
              B         vH               v        F             H
              s         ip               l        o             p
              m         Jh               J        k             h
              I         II               I        I             I
          TGCGGTGAATGTGAGCCAGATGAAGGATGTGGCTGTGATGGTGATGATGGTGATGGTGAT
541      ----------+---------+---------+---------+---------+---------+ 600
          ACGCCACTTACACTCGGTCTACTTCCTACACCGACACTACCACTACTACCACTACCACTA N S         N   S       N  S    N
                                  l a         l   a B     l  Ba   l
              H     H      H    H BaDu        a   u Ds    BaDsu   a
              P     p      p    p cIp3        I   3 pp    cIpp3   I
```

FIG. 9B

```
            h     h     h     h        1InA              I       A  nH    1InHA    I
            I     I     I     I        IIII              I       I  II    IIIII    I
           GGTGATGGTGATGATGATGATGAGCATGATCACGAACATGGACACGATCATGATCATGAA
      601  ----------+----------+----------+----------+----------+----------+  660
           CCACTACCACTACTACTACTACTCGTACTAGTGCTTGTACCTGTGCTAGTACTAGTACTT

N                       S                    N
                 B    M     l                  M    aM                   l
                 b    b     a                  b    ubD                  a
                 v    o     I                  o    3op                  I
                 I    I     I                  I    AIn                  I
                 I    I     I                  I    III                  I
           GACGGACAAGAACATGAAGATGAAGATGGACACGATCACGGACACGAGCATGAAGATGGA
      661  ----------+----------+----------+----------+----------+----------+  720
           CTGCCTGTTCTTGTACTTCTACTTCTACCTGTGCTAGTGCCTGTGCTCGTACTTCTACCT

N S         S            N
                 M           l a         a        B   l
                 Hb          BaDu       BuD       s   a
                 po          cIp3       c3p       p   I
                 hI          1InA       1An       H   I
                 II          IIII        III      I   I
           CACGAACATCATCACCATGATCACGATGATCATCATGAACACGATGATGATAAAGCA
      721  ----------+----------+----------+----------+----------+----------+  780
           GTGCTTGTAGTAGTGGTACTAGTGCTACTAGTAGTAGTACTTGTGCTACTACTATTTCGT

C                      T                            C
                 Av     S                s       M                   Av
                 1i     s                p       a                   1i
                 uJ     p                E       e                   uJ
                 II     I                I       I                   II
           AAAATAGCTAATATTGGTTCTACAAATATAATTGCTAGATTTTGGTTAGCAATGATAGCT
      781  ----------+----------+----------+----------+----------+----------+  840
           TTTTATCGATTATAACCAAGATGTTTATATTAACGATCTAAAACCAATCGTTACTATCGA

M                              S
                    a                              s
                    e                              p
                    I                              I
           ACTATTTCTAGCATATTATTTCTATGAAAATATTGATATAACTGTTTTGATTTAGAAACA
      841  ----------+----------+----------+----------+----------+----------+  900
           TGATAAAGATCGTATAATAAAGATACTTTTATAACTATATTGACAAAACTAAATCTTTGT

A    N
                      f    1N       T
                      l    as       s              MD
                      I    Ip       p              sr
                      I    IH       E              ea
                      I    II       I              II
           GCATAGCACATGTAAAAATAATTTAGAAATGTTTTTACATTTAAAGGTTTACATATTCTA
      901  ----------+----------+----------+----------+----------+----------+  960
           CGTATCGTGTACATTTTTATTAAATCTTTACAAAAATGTAAATTTCCAAATGTATAAGAT
                      D                            M
                      d                            s
                      e                            e
```

FIG. 9C

```
              I                                      I
     TTTTATGCTTAGAAAAAAATACTTTATAATAGTTGAAAATCTTAAACTATATCTTTCTAT
961  ----------+---------+---------+---------+---------+---------+ 1020
     AAAATACGAATCTTTTTTTATGAAATATTATCAACTTTTAGAATTTGATATAGAAAGATA

B
      T          M                        M   E  T    sH
      s          bMV                      b   c  s    pp
      P          oss                      o   o  p    Ma
      E          Iep                      I   R  E    II
      I          III                      I   I  I    II
                 //
     TTGGAATTGTAATATATTAATCAATCTTCTAAAAAAAAAAAAAAAGGAATTCTTCCGGAT
1021 ----------+---------+---------+---------+---------+---------+ 1080
     AACCTTAACATTATATAATTAGTTAGAAGATTTTTTTTTTTTTTCCTTAAGAAGGCCTA NF
                                  M                           1nN
      MD         D        CT      a      M         B          ausS
      sr         d        la      e      n         b          I4pp
      ea         e        aq      I      l         v          IHHh
      II         I        II      I      I         I          IIII
                                   /                          //
     TTTTAAACCCCGTCTGAGCAATAATCGATGAACGTGCGAGTTATTGAGGGTGCATGCTGC
1081 ----------+---------+---------+---------+---------+---------+ 1140
     AAAATTTGGGGCAGACTCGTTATTAGCTACTTGCACGCTCAATAACTCCCACGTACGACG C                              E T
              Av                             c s
              l1                             o p
              uJ                             R E
              II                             I I
               /
     ACTCCACACCAGAGCTTTGACGACACCACTCGTTTCAATGGGGGAATTC
1141 ----------+---------+---------+---------+-------- 1189
     TGAGGTGTGGTCTCGAAACTGCTGTGGTGAGCAAAGTTACCCCCTTAAG
```

FIG. 9D

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2814 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 1617..2813

( x i ) SEQUENCE DESCRIPTION: SEQ ID NO:1:

```
CTCTTATTAA ATTTAATTTA TTTATTTGCG GTGTTGGTGA TACACTATTC TGTACAATCG      60

GAGATGATTG AAATATGTCCT TGTGATGTTT GGTTAGCAGA TGAAGATTGC AGTATATTTT    120

GTGATGTCTG TATTTGTTGT TGCTGCGATT GCTGTTGTGA TTGTTGTTGG TGTGGTTGTG    180

ATGATTGTTG GGATTGCTGC TGGGATTGTG GTATTTGATT TTGTGGTGAA TGTTGGTTTA    240

AATGCCCTTG TGTATGATTT ATATTTTGCA TTTGAATATT ACGGTTTTGA TTTTGATTAA    300

CTAAATGCTG CATTATTTGC TGCTGCTGCC ATATTGTACT GGGTTGATTT GTTCGTACTA    360

CTCTTGGATT TATTAAATGT TCTGGCCTAC CATTTATCAT AGCCATCTGC ATTTGCGGAT    420

TATTCACATA AATGGATTGA TCAGTCATTT GAGATCTCAT AATATGTCCA TTATGACCCA    480

TCATTATTCC ATCGTTTTGC ATATCTCCCA TAGTTTTTGC TTGATTGAAA AACATAATTT    540

GTGGATGAGT GTCGGATTGA ATTTGGCCAT TGTATCCTGC AATACTAGGT GAAGTATTTC    600

TTGAAGTATT ATTTTGTTGA GAAAGTGGAC CATCGGTAGG TGAATTAGGG GAATTTTGAT    660

GAGCCACTTT TGAAATGCCG CGTTTAGTAT CATTATGATT ATTTTTCGGA GAAAGAGCAT    720

TTCTAACTCC TTGTGGAGAT AAAATCTGAA AAGTGGATGA ATCTTGTGAT TGAAGTCGTT    780

CTTGATCTTG ATGTGTCATC ATAAGGCGTT TTTTATTCTG CTGTTCAAGA AACATAAGCT    840

GCATTTGATA ATCTTCAAGA GTATGATTAT TAGGATTTGT CGGGCAGTTT TGCTGAGACG    900

GTAATATATT TCCATAAAAA TCATTAGGCC CCATTTCATT TCCATCACCC GTCATTATTG    960

ATGAAGGAAG ACATTGATTT GAAATTTGCC CTTTAGGAAT ATTTAGAACT CTTTGTTGTT   1020

GATTCGAAAA ACCCTGTGTA TATTTTTGCA ATTGTCTCTG TTGCATAGAG GGCGTTTGTG   1080

ATTGAAATGC AGTAAATTGC TGTTGTGTAA GACCGACCGG GTTAATTCCG GTTAAGAGGC   1140

AAGCACAAGT AGTACAAGTA GCACAAGATG AGATTAAGGA GGAACACCTT TTGGCTTTCA   1200

TTGTGAAGGA CAAACATGAT GATGAGAATG AATGCAAAAA AAGGCTCGAG GAATATTGTA   1260

AAGAGTTGAA GAAAGCAGAT GAGAATTTCA GTGTGAATGA GAAAGTTAAA GGACTTTGTG   1320
```

```
ATGATAAAAA ACGAGACGAA AAATGCAAAG AACTGAAAAA AAAAGTTAAA GATGAATTGG    1380

GAACTTTTGA TACGGATCTT GAAGCATCGG TAGATGACAT AGAAGATGAA GGAGTTTGTA    1440

AAAAACATGA AGAAAATGT ATACTTTTAG AGGAAGCAGA CCCAAATAGT CTTAAGGAGA     1500

ACTGTGTCAA GTTGAGGGAA GGATGTTACG AATTGAAGCG TAAAAAGGTG GCAGAGGAGC    1560

TCCTTTTGAG GGCGCTCGGA GGGGATGCTA AGATGAAGC TAAATGTAAA GAAAAG         1616
```

| ATG | AAA | ACT | GTT | TGC | CCA | ATG | TTA | AGC | CGA | GAA | AGT | GAC | GAG | CTG | ATG | 1664 |
|-----|-----|-----|-----|-----|-----|-----|-----|-----|-----|-----|-----|-----|-----|-----|-----|------|
| Met | Lys | Thr | Val | Cys | Pro | Met | Leu | Ser | Arg | Glu | Ser | Asp | Glu | Leu | Met | |
| 1 | | | | 5 | | | | | 10 | | | | | 15 | | |

| TTT | TTC | TGC | CTT | GAT | TCG | GAT | GGA | ACG | TGT | AAA | GCG | CTG | AAA | ACA | AAA | 1712 |
|-----|-----|-----|-----|-----|-----|-----|-----|-----|-----|-----|-----|-----|-----|-----|-----|------|
| Phe | Phe | Cys | Leu | Asp | Ser | Asp | Gly | Thr | Cys | Lys | Ala | Leu | Lys | Thr | Lys | |
| | | | 20 | | | | | 25 | | | | | 30 | | | |

| TCA | GAA | GAA | GTT | TGC | CTG | CCT | TTA | AAA | GAA | AAG | CTT | AAA | GAT | GGC | GAA | 1760 |
|-----|-----|-----|-----|-----|-----|-----|-----|-----|-----|-----|-----|-----|-----|-----|-----|------|
| Ser | Glu | Glu | Val | Cys | Leu | Pro | Leu | Lys | Glu | Lys | Leu | Lys | Asp | Gly | Glu | |
| | | 35 | | | | | 40 | | | | | 45 | | | | |

| TTA | AAG | GAA | AAA | TGT | CAT | GAA | AGA | CTT | GAG | AAA | TGT | CAT | TTT | TAC | AAA | 1808 |
|-----|-----|-----|-----|-----|-----|-----|-----|-----|-----|-----|-----|-----|-----|-----|-----|------|
| Leu | Lys | Glu | Lys | Cys | His | Glu | Arg | Leu | Glu | Lys | Cys | His | Phe | Tyr | Lys | |
| | 50 | | | | | 55 | | | | | 60 | | | | | |

| GAA | GCG | TGT | ACT | GAA | ACA | AAG | TGT | GAT | GAG | GAT | ATG | AAG | CAA | TGC | AAG | 1856 |
|-----|-----|-----|-----|-----|-----|-----|-----|-----|-----|-----|-----|-----|-----|-----|-----|------|
| Glu | Ala | Cys | Thr | Glu | Thr | Lys | Cys | Asp | Glu | Asp | Met | Lys | Gln | Cys | Lys | |
| 65 | | | | | 70 | | | | | 75 | | | | | 80 | |

| GAA | AAA | GGA | TTC | ACA | TAT | AAA | GCG | CCG | GAA | TCT | GAT | TTT | AGT | CCT | GTC | 1904 |
|-----|-----|-----|-----|-----|-----|-----|-----|-----|-----|-----|-----|-----|-----|-----|-----|------|
| Glu | Lys | Gly | Phe | Thr | Tyr | Lys | Ala | Pro | Glu | Ser | Asp | Phe | Ser | Pro | Val | |
| | | | | 85 | | | | | 90 | | | | | 95 | | |

| AAG | CCG | AAG | GCG | TCG | TTG | TTG | AGA | AGT | ATT | GGG | TTG | GAT | GAT | GTG | TAT | 1952 |
|-----|-----|-----|-----|-----|-----|-----|-----|-----|-----|-----|-----|-----|-----|-----|-----|------|
| Lys | Pro | Lys | Ala | Ser | Leu | Leu | Arg | Ser | Ile | Gly | Leu | Asp | Asp | Val | Tyr | |
| | | | 100 | | | | | 105 | | | | | 110 | | | |

| AAA | AAG | GCT | GAA | AAA | GAA | GGA | ATT | ATT | ATT | GGA | AAA | TCA | GGA | GTG | GAT | 2000 |
|-----|-----|-----|-----|-----|-----|-----|-----|-----|-----|-----|-----|-----|-----|-----|-----|------|
| Lys | Lys | Ala | Glu | Lys | Glu | Gly | Ile | Ile | Ile | Gly | Lys | Ser | Gly | Val | Asp | |
| | | 115 | | | | | 120 | | | | | 125 | | | | |

| CTA | CCA | AGG | AAG | TCA | GGT | ACA | AAA | TTT | CTG | CAA | GAT | CTC | TTG | CTA | CTG | 2048 |
|-----|-----|-----|-----|-----|-----|-----|-----|-----|-----|-----|-----|-----|-----|-----|-----|------|
| Leu | Pro | Arg | Lys | Ser | Gly | Thr | Lys | Phe | Leu | Gln | Asp | Leu | Leu | Leu | Leu | |
| 130 | | | | | 135 | | | | | 140 | | | | | | |

| TTG | AGC | AGA | GAT | GAG | AAT | GAT | GCA | GGG | AAG | AAA | TGC | GGT | AAA | GCG | TTA | 2096 |
|-----|-----|-----|-----|-----|-----|-----|-----|-----|-----|-----|-----|-----|-----|-----|-----|------|
| Leu | Ser | Arg | Asp | Glu | Asn | Asp | Ala | Gly | Lys | Lys | Cys | Gly | Lys | Ala | Leu | |
| 145 | | | | | 150 | | | | | 155 | | | | | 160 | |

| GGA | AAA | TGT | GAA | ACT | TCT | AAG | TAT | TTG | AAT | ACT | GAT | TTG | ATG | GAG | TTA | 2144 |
|-----|-----|-----|-----|-----|-----|-----|-----|-----|-----|-----|-----|-----|-----|-----|-----|------|
| Gly | Lys | Cys | Glu | Thr | Ser | Lys | Tyr | Leu | Asn | Thr | Asp | Leu | Met | Glu | Leu | |
| | | | | 165 | | | | | 170 | | | | | 175 | | |

| TGC | AAA | GAT | GCT | GAT | AAA | GAA | AAT | AAA | TGC | AAA | AAA | AAG | CTA | GAT | GTA | 2192 |
|-----|-----|-----|-----|-----|-----|-----|-----|-----|-----|-----|-----|-----|-----|-----|-----|------|
| Cys | Lys | Asp | Ala | Asp | Lys | Glu | Asn | Lys | Cys | Lys | Lys | Lys | Leu | Asp | Val | |
| | | | 180 | | | | | 185 | | | | | 190 | | | |

| AAA | GAA | AGA | TGT | ACA | AAA | CTC | AAG | TTA | AAT | CTT | TAT | GTG | AAA | GGG | TTG | 2240 |
|-----|-----|-----|-----|-----|-----|-----|-----|-----|-----|-----|-----|-----|-----|-----|-----|------|
| Lys | Glu | Arg | Cys | Thr | Lys | Leu | Lys | Leu | Asn | Leu | Tyr | Val | Lys | Gly | Leu | |
| | | 195 | | | | | 200 | | | | | 205 | | | | |

| TCT | ACG | GAG | TTT | AAA | GAA | GAT | AAA | AAA | TCA | CAT | CTT | TTA | TCG | TGG | GGA | 2288 |
|-----|-----|-----|-----|-----|-----|-----|-----|-----|-----|-----|-----|-----|-----|-----|-----|------|
| Ser | Thr | Glu | Phe | Lys | Glu | Asp | Lys | Lys | Ser | His | Leu | Leu | Ser | Trp | Gly | |
| 210 | | | | | 215 | | | | | 220 | | | | | | |

| CAG | CTT | CCA | ACA | TTA | TTT | ACG | AAG | GGA | GAG | TGT | GCA | GAA | CTT | GAG | TCG | 2336 |
|-----|-----|-----|-----|-----|-----|-----|-----|-----|-----|-----|-----|-----|-----|-----|-----|------|
| Gln | Leu | Pro | Thr | Leu | Phe | Thr | Lys | Gly | Glu | Cys | Ala | Glu | Leu | Glu | Ser | |
| 225 | | | | | 230 | | | | | 235 | | | | | 240 | |

| GAA | TGT | TTC | TAT | TTA | GAA | AAT | GCG | TGT | AAA | GAT | AAT | GAG | ATT | GGT | GAA | 2384 |
|-----|-----|-----|-----|-----|-----|-----|-----|-----|-----|-----|-----|-----|-----|-----|-----|------|
| Glu | Cys | Phe | Tyr | Leu | Glu | Asn | Ala | Cys | Lys | Asp | Asn | Glu | Ile | Gly | Glu | |
| | | | | 245 | | | | | 250 | | | | | 255 | | |

| GCG | TGT | CAA | AAT | CTA | CGA | TCA | GCG | TGC | TAT | AAA | AAG | GGA | CAA | GAC | AGG | 2432 |
|-----|-----|-----|-----|-----|-----|-----|-----|-----|-----|-----|-----|-----|-----|-----|-----|------|
| Ala | Cys | Gln | Asn | Leu | Arg | Ser | Ala | Cys | Tyr | Lys | Lys | Gly | Gln | Asp | Arg | |
| | | | 260 | | | | | 265 | | | | | 270 | | | |

| ATG | TTG | AAT | AAG | TTC | TTT | CAA | AAG | GAA | TTG | AAG | GGA | AAG | CTT | GGT | CAT | 2480 |
|-----|-----|-----|-----|-----|-----|-----|-----|-----|-----|-----|-----|-----|-----|-----|-----|------|
| Met | Leu | Asn | Lys | Phe | Phe | Gln | Lys | Glu | Leu | Lys | Gly | Lys | Leu | Gly | His | |
| | | 275 | | | | | 280 | | | | | 285 | | | | |

| | | | | | | | | | | | | | | | | |
|---|---|---|---|---|---|---|---|---|---|---|---|---|---|---|---|---|
| GTA | AGA | TTT | TAT | AGC | GAT | CCT | AAA | GAT | TGT | AAA | AAA | TAT | GTG | GTA | GAA | 2528 |
| Val | Arg<br>290 | Phe | Tyr | Ser | Asp | Pro<br>295 | Lys | Asp | Cys | Lys | Lys<br>300 | Tyr | Val | Val | Glu | |
| AAC | TGT | ACA | AAA | CTT | AAA | AAA | GAT | AAA | AGA | TAC | CTT | TCA | AAA | TGT | CTT | 2576 |
| Asn<br>305 | Cys | Thr | Lys | Leu<br>310 | Lys | Lys | Asp | Lys | Arg<br>315 | Tyr | Leu | Ser | Lys | Cys<br>320 | Leu | |
| TAT | CCT | AAA | GAA | CTA | TGT | TAT | GGG | CTT | TCA | AAT | GAT | ATT | TTT | CTC | CAA | 2624 |
| Tyr | Pro | Lys | Glu | Leu<br>325 | Cys | Tyr | Gly | Leu | Ser<br>330 | Asn | Asp | Ile | Phe | Leu<br>335 | Gln | |
| TCC | AAA | GAG | TTA | AGT | TCG | CTT | TTA | GAT | GAT | CAG | AGA | GAT | TTT | CCA | TTT | 2672 |
| Ser | Lys | Glu | Leu<br>340 | Ser | Ser | Leu | Leu | Asp<br>345 | Asp | Gln | Arg | Asp | Phe<br>350 | Pro | Phe | |
| GAA | AAG | GAT | TGT | CTT | GAA | TTG | GGA | GAG | AAG | TGT | GAT | CAA | CTT | AGT | AGT | 2720 |
| Glu | Lys | Asp<br>355 | Cys | Leu | Glu | Leu | Gly<br>360 | Glu | Lys | Cys | Asp | Gln<br>365 | Leu | Ser | Ser | |
| GAT | TCA | TTA | TTG | AAT | TTA | GAA | AAG | TGT | ATA | ACA | TTG | AAA | AGA | CGC | TGT | 2768 |
| Asp | Ser<br>370 | Leu | Leu | Asn | Leu | Glu<br>375 | Lys | Cys | Ile | Thr | Leu<br>380 | Lys | Arg | Arg | Cys | |
| GAA | TAT | TTT | GAC | GTT | ACA | GAA | AGA | TTT | AGA | AAA | GTA | TTT | TTA | AAA | | 2813 |
| Glu | Tyr | Phe | Asp | Val | Thr<br>390 | Glu | Arg | Phe | Arg | Lys<br>395 | Val | Phe | Leu | Lys | | |
| A | | | | | | | | | | | | | | | | 2814 |

(2) INFORMATION FOR SEQ ID NO:2:

(i) SEQUENCE CHARACTERISTICS:
  (A) LENGTH: 399 amino acids
  (B) TYPE: amino acid
  (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met<br>1 | Lys | Thr | Val | Cys<br>5 | Pro | Met | Leu | Ser | Arg<br>10 | Glu | Ser | Asp | Glu | Leu<br>15 | Met |
| Phe | Phe | Cys | Leu<br>20 | Asp | Ser | Asp | Gly | Thr<br>25 | Cys | Lys | Ala | Leu | Lys<br>30 | Thr | Lys |
| Ser | Glu | Glu<br>35 | Val | Cys | Leu | Pro | Leu<br>40 | Lys | Glu | Lys | Leu | Lys<br>45 | Asp | Gly | Glu |
| Leu | Lys<br>50 | Glu | Lys | Cys | His | Glu<br>55 | Arg | Leu | Glu | Lys | Cys<br>60 | His | Phe | Tyr | Lys |
| Glu<br>65 | Ala | Cys | Thr | Glu | Thr<br>70 | Lys | Cys | Asp | Glu | Asp<br>75 | Met | Lys | Gln | Cys | Lys<br>80 |
| Glu | Lys | Gly | Phe | Thr<br>85 | Tyr | Lys | Ala | Pro | Glu<br>90 | Ser | Asp | Phe | Ser | Pro<br>95 | Val |
| Lys | Pro | Lys | Ala<br>100 | Ser | Leu | Leu | Arg | Ser<br>105 | Ile | Gly | Leu | Asp | Asp<br>110 | Val | Tyr |
| Lys | Lys | Ala<br>115 | Glu | Lys | Glu | Gly | Ile<br>120 | Ile | Ile | Gly | Lys | Ser<br>125 | Gly | Val | Asp |
| Leu | Pro<br>130 | Arg | Lys | Ser | Gly | Thr<br>135 | Lys | Phe | Leu | Gln | Asp<br>140 | Leu | Leu | Leu | Leu |
| Leu<br>145 | Ser | Arg | Asp | Glu | Asn<br>150 | Asp | Ala | Gly | Lys | Lys<br>155 | Cys | Gly | Lys | Ala | Leu<br>160 |
| Gly | Lys | Cys | Glu | Thr<br>165 | Ser | Lys | Tyr | Leu | Asn<br>170 | Thr | Asp | Leu | Met | Glu<br>175 | Leu |
| Cys | Lys | Asp | Ala<br>180 | Asp | Lys | Glu | Asn | Lys<br>185 | Cys | Lys | Lys | Leu | Asp<br>190 | Val | |
| Lys | Glu | Arg<br>195 | Cys | Thr | Lys | Leu | Lys<br>200 | Leu | Asn | Leu | Tyr | Val<br>205 | Lys | Gly | Leu |
| Ser | Thr | Glu | Phe | Lys | Glu | Asp | Lys | Lys | Ser | His | Leu | Leu | Ser | Trp | Gly |

|              |              |              |              |              |              |              |              |              |              |              |              |              |              |              |
|---|---|---|---|---|---|---|---|---|---|---|---|---|---|---|

```
                210                            215                            220
Gln   Leu   Pro   Thr   Leu   Phe   Thr   Lys   Gly   Glu   Cys   Ala   Glu   Leu   Glu   Ser
225                           230                           235                           240

Glu   Cys   Phe   Tyr   Leu   Glu   Asn   Ala   Cys   Lys   Asp   Asn   Glu   Ile   Gly   Glu
                        245                           250                           255

Ala   Cys   Gln   Asn   Leu   Arg   Ser   Ala   Cys   Tyr   Lys   Lys   Gly   Gln   Asp   Arg
                  260                           265                           270

Met   Leu   Asn   Lys   Phe   Phe   Gln   Lys   Glu   Leu   Lys   Gly   Lys   Leu   Gly   His
            275                           280                           285

Val   Arg   Phe   Tyr   Ser   Asp   Pro   Lys   Asp   Cys   Lys   Lys   Tyr   Val   Val   Glu
      290                           295                           300

Asn   Cys   Thr   Lys   Leu   Lys   Lys   Asp   Lys   Arg   Tyr   Leu   Ser   Lys   Cys   Leu
305                           310                           315                           320

Tyr   Pro   Lys   Glu   Leu   Cys   Tyr   Gly   Leu   Ser   Asn   Asp   Ile   Phe   Leu   Gln
                        325                           330                           335

Ser   Lys   Glu   Leu   Ser   Ser   Leu   Leu   Asp   Asp   Gln   Arg   Asp   Phe   Pro   Phe
                  340                           345                           350

Glu   Lys   Asp   Cys   Leu   Glu   Leu   Gly   Glu   Lys   Cys   Asp   Gln   Leu   Ser   Ser
            355                           360                           365

Asp   Ser   Leu   Leu   Asn   Leu   Glu   Lys   Cys   Ile   Thr   Leu   Lys   Arg   Arg   Cys
      370                           375                           380

Glu   Tyr   Phe   Asp   Val   Thr   Glu   Arg   Phe   Arg   Lys   Val   Phe   Leu   Lys
385                           390                           395
```

( 2 ) INFORMATION FOR SEQ ID NO:3:

( i ) SEQUENCE CHARACTERISTICS:
        ( A ) LENGTH: 1448 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
GTCGACTCTA  GAGGATCCCC  GGGTACCGAG  CTCGAATTCC  TTTTTGCGCA  ACTTAGTTGT     60
ATTTTAGTTT  ATTCAATAGC  AGAAAGGGAT  TTCATGTCAT  TAGATGAAAT  ATATGAAGGA    120
GGCGATATAA  GTTTGATCA   TGAAAAACTC  GAATTTAACG  AATATATCAA  GTTTTACAAA    180
TGCTTGAAAA  GGCAAAAAAT  ATTGGGAACC  GGCTTTGTTG  ATAGAACCAA  AGATTTTCT     240
AATAGACGAT  ATGAAGGGAG  AATTGAGTTA  AATCATTTGG  GGAGACGCCC  AGGAGTCGAC    300
TATTTTAGGA  AAGGTGGGGA  TGTTTTTACT  GATGGTTATC  CTCGTGGAGG  TCATTTGATC    360
GAGGATGAGT  TGTCCGAAGA  GGCGGCAATG  GCACGGCCGG  TTAAGAGGCA  AGCACAAGTA    420
GTACAAGTAA  GCACAAGATG  AGATTAAGGA  GGAACACCTT  TTGGCTTTCA  TTGTGAAGGA    480
CAAACATGAT  GATGAGAATG  AATGCAAAAA  AAGGCTCGAG  GAATATTGTA  AGAGTTGAA     540
GAAAGCAGAT  GAGAATTTCA  GTGTGAATGA  AAAGTTAAA   GGACTTTGTG  ATGATAAAAA    600
ACGAGACGAA  AAATGCAAAG  AACTGAAAAA  AAAAGTTGGG  GATGAATTGG  AACTTTTGA     660
TACGGATCTT  GAAGCATCGG  TAGATGACAT  AGAAGATGAA  GGAGTTTGTA  AAAAACATGA    720
AGAAAAATGT  ATACTTTTAG  AGGAAGCAGA  CCCAAATAGT  CTTAAGGAGA  ACTGTGTCAA    780
GTTGAGGGAA  GGATGTTACG  AATTGAAGCG  TAAAAAGGTG  GCAGAGGAGC  TCCTTTTGAG    840
GGCGCTCGGA  AAGGAAGCTA  AGAAGAAGT   TAAATGTAAA  GCAGAGATGA  AAAAGGTTTG    900
```

```
CCCAGTGTTA  AGCCGAGAAA  GCGACGAATT  GATGTTTTTG  TGCCTTGATT  CGGATGGAAC    960

GTGTCAGCGC  TGAAAAAAAA  ATCAGAAGAA  GTTTGCCAGC  TTTTAAAGAA  AGCTTAAAGA   1020

TGGCGAATTA  AAGGAAAAAT  GTCATGAAAG  ACTTGAGAAA  TGTCATTTTT  ACGGAGAAGC   1080

GTGTGATAAA  ACAAATGTG   ATGAGGATAA  GGATCAATGC  GAGAAAAAAG  AAATCACATA   1140

TAAGCGCCAG  AATCTGATTC  TAGTCCTGTC  AAGCCGAAGA  CGTCGTTGTT  GAGAAGTATT   1200

GGGTTGGATG  ATGTGTATAA  AAGAGCTGAA  AAGAAGGAA   TTATTATTGG  AAAATCAGGA   1260

GTGGATCTAC  CAAGGAAGTC  AGGTACAAAA  TTTCTGCAAG  ATCTCTTGCT  AGTCTTGAGC   1320

AGAGATGAGA  ATGATAAGGA  TGCAGGGAAG  AAATGCGAAA  AAGCGTTAAA  AAAATGTGAA   1380

ACTTCTAGTA  TTTGAATACT  GATTTGATGG  AGTTATGCAA  AGATGCTGAT  AAACAAAAAA   1440

AGGAATTC                                                                1448
```

(2) INFORMATION FOR SEQ ID NO:4:

(i) SEQUENCE CHARACTERISTICS:
        (A) LENGTH: 1189 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:4:

```
GAATTCCTTT  TTTTTTTCAT  AATGGGTTTT  TTATTTGTTA  CGTTTTTATT  TTCTATAATA     60

GCTTTAATAA  ATGCTATTGA  AATTTGTAT   CCTAAAGCTG  GTGATAAATT  GCAAGCCGGT    120

TTACATGAAG  TTAAATGGAC  TACTGAAAGT  GCCACTTCTA  TAGATAAGGT  TAATGTGTTT    180

CTTTTTAATG  ACAAGGAATC  CCCCCCTTTT  TACCTTCAGC  TAGCAGCTGA  TGTTACTTTT    240

TCTAATGGAA  AAGTTAGCGT  TCCTATACCT  TATAATGTCG  TTCCTGGTCC  TGATTATACT    300

ATTTTACTTA  CTGCGAAAAA  TCCATATGAT  GTTTACGCTA  CTAGTGGTTC  TTTTAGTATT    360

GCAGAGTCTA  AACTTTCAGC  CGACGCTTGT  GTTAATTTTC  TTAATGAAGA  TGGTTCATCC    420

ACTATTGGTC  CTGTACCTGG  TAAAGTTAAG  CCTGTTTCTA  CTGATCTTGT  ATCACCTCTG    480

CCACCTGCAC  CTCCTGATGA  AGACTTTGAA  GATTGTGACG  AATGTGATGA  ATGTGAGGAA    540

TGCGGTGAAT  GTGAGCCAGA  TGAAGGATGT  GGCTGTGATG  GTGATGATGG  TGATGGTGAT    600

GGTGATGGTG  ATGATGATGA  TGAGCATGAT  CACGAACATG  GACACGATCA  TGATCATGAA    660

GACGGACAAG  AACATGAAGA  TGAAGATGGA  CACGATCACG  GACACGAGCA  TGAAGATGGA    720

CACGAACATC  ATCACCATGA  TCACGATGAT  CATCATCATG  AACACGATGA  TGATAAAGCA    780

AAAATAGCTA  ATATTGGTTC  TACAAATATA  ATTGCTAGAT  TTGGTTAGC   AATGATAGCT    840

ACTATTTCTA  GCATATTATT  TCTATGAAAA  TATTGATATA  ACTGTTTTGA  TTTAGAAACA    900

GCATAGCACA  TGTAAAAATA  ATTTAGAAAT  GTTTTTACAT  TTAAAGGTTT  ACATATTCTA    960

TTTTATGCTT  AGAAAAAAAT  ACTTTATAAT  AGTTGAAAAT  CTTAAACTAT  ATCTTTCTAT   1020

TTGGAATTGT  AATATATTAA  TCAATCTTCT  AAAAAAAAAA  AAAAAGGAAT  TCTTCCGGAT   1080

TTTTAAACCC  CGTCTGAGCA  ATAATCGATG  AACGTGCGAG  TTATTGAGGG  TGCATGCTGC   1140

ACTCCACACC  AGAGCTTTGA  CGACACCACT  CGTTTCAATG  GGGGAATTC                1189
```

MOLECULAR CLONING OF ANTIGENS SHARED BY RAT- AND HUMAN-DERIVED *PNEUMOCYSTIS CARINII*

GOVERNMENT SUPPORT

The invention described herein was supported in whole or in part by Grant No. K08-HL01916 and Grant No. PO1HL43510 from the National Institutes of Health. The U.S. Government has certain rights in the invention.

RELATED APPLICATIONS

This is a continuation-in-part of U.S. application Ser. No. 07/768,166, filed on Sep. 30, 1991, abandoned. The teachings of U.S. Ser. No. 07/768,166 are incorporated herein by reference.

BACKGROUND

*Pneumocystis carinii* (Pc) is an important and potentially lethal pulmonary pathogen in many immuno-compromised individuals, most notably those with the Acquired Immunodeficiency Syndrome (AIDS). Over 80% of individuals with AIDS will develop Pc pneumonitis or pneumonia (PCP) over the course of their lives without specific antibiotic prophylaxis. PCP is the most significant immediate cause of death in AIDS. PCP is also a serious complication in cancer and transplant patients and malnourished children. (Hughes, W. T., *Pneumocystis carinii Pneumonitis*, New York: CRC Press, 1987; Kovacs, J. A. et al. (1984) *Annals of Internal Medicine* 100:663–671; Murray, J. F. et al. (1984) *New England J. Med.* 310:1682–1688; Goedert, J. J. et al. (1987) *JAMA* 257(3):331–4; Bonagura, V. R. et al. (1989) *Clin. Immun. Immunopath.* 51(2):216–31; Mamedov, N. A. et al. (1991) *Mikrobiol. Epidemiol. Immunobiol.* 0(2);32–34; Maddison, S. E. et al. (1982) *J. Clin. Microbiol.* 15(6):1029–1035; Jarowenko, M. et al. (1986) *Transplantation* 41(4):436–442)

Standard prophytaxis with trimethoprim-sulfamethoxazole (TMP-SMX), pentamidine, isethionate, Dapsone and other newer modalities have reduced the mortality and morbidity due to PCP. However, therapy with these agents is frequently attended by adverse reactions, such as allergic reactions, to these drugs. Most notably, over half of patients with AIDS will have adverse reactions to one or more of these agents. This has limited the utility of both prophylactic agents and therapies in the treatment of PCP in the AIDS patients. In transplant patients, synergistic toxicity to the kidneys has been observed between TMP-SMX and the immunosuppressive drugs cyclosporin A and azathioprine. (Fishman, J. A., *Medical Times*, 1989, pp. 21–34; Fishman, J. A., Pulmonary Diseases and Disorders. In: *Pneumocystis carinii Pneumonitis* (A. P. Fishman, ed.). New York: McGraw Hill, 1991, in press; Masur, H. (1989) *J. Protozoology* 36(1):70–74; Matsumoto, Y. et al. (1991) Abstract WS1, *Program and Abstracts of the 44th Annual Meeting of the Society of Protozoologists, Jun. 28–Jul. 2*, 1991:46) It has been stated that: "Under these circumstances, an understanding of pneumocystosis is urgent and basic studies of this organism are necessary" (Nakamura, Y. et al. (1989) 36(1):58S–60S).

However, studies of the pathogenesis of PCP have been hindered by the absence of a continuous culture system for the growth of human or animal Pc, and by the contamination of Pc preparations by host proteins and nucleic acids. Despite some improvements in both the animal and tissue culture systems for the growth and purification of Pc, dissection of the interactions of Pc with the cells and tissues and the immune system of the host has been difficult. (Bartlett, M. S. et al. (1988) *J. Clin. Microbiol.* 26:1100–1102)

SUMMARY OF THE INVENTION

The present invention is based on the isolation of a gene encoding an antigen present on *Pneumocystis carinii* (Pc) from both rat and human sources. As described herein, a 2814 base pair (bp) cDNA insert has been isolated from a cDNA expression library derived from rat Pc (i.e., from Pc obtained from rat tissue) and analyzed. The cloned DNA, designated JFBIg10 DNA, has been shown to encode a Pc protein which shares epitopes with a major surface antigen of approximately 110–120 kilodaltons (kD) found on both rat and human Pc, referred to herein as gp116 major surface antigen; it is a major surface antigen in terms of quantity and immunoreactivity. Sequence analysis of the 2814 bp cDNA insert shows that it contains a 1197 bp open reading frame encoding a 399 amino acid peptide. The gene has been shown to hybridize only to Pc DNA and not to potential contaminants, including human, rat, mink, *E. coli*, yeast, and bacteriophage lambda DNAs. The nucleotide sequence and deduced amino acid sequence have been shown to exhibit no significant homology with previously published genes or peptides in the GenBank or Swissprot databases.

Diagnostic probes for polymerase chain reaction (PCR) derived from the JFBIg10 DNA have been shown to detect nucleotide sequences at high stringency of hybridization to DNAs derived from both rat and human Pc. These PCR probes do not detect sequences in uninfected rat- or human-derived materials. Over 2000 bp, or 90% of the homologous human-derived sequence, have been demonstrated to be identical to that of the rat JFBIg10 antigen gene. No differences between the rat- and human-derived nucleotide sequences have been detected to date using multiple human-derived samples as sources for the material probed.

In addition, this invention is based on the cloning and nucleotide sequence of a fragment of genomic DNA from rat Pc, which hybridizes to a nucleic acid probe derived from the JFBIg10 gene. This cloned DNA, designated JS7-2A3U DNA, is a member of a family of nucleotide sequences which are homologous to the JFBIg10 DNA sequence.

This invention is also based on the cloning and nucleotide sequence of another cDNA derived from rat Pc, designated JFSIg2 DNA, which also encodes a surface antigen of rat Pc.

Thus, this invention relates to JFBIg10 DNA, which encodes an antigen of mammalian Pc, particularly of rodent and human origin, which shares epitopes with the gp116 major surface antigen of rat and human Pc; to homologous DNA sequences, and in particular, JS7-2A3U DNA; and to other Pc DNA sequences encoding surface antigens of mammalian Pc, and in particular, JFSIg2 DNA. RNA and translated protein products of the above-mentioned DNAs are also included. Chimeric molecules containing all or a portion or portions of the above-mentioned DNAs, or of their encoded RNAs or proteins are included.

This invention further relates to polyclonal and monoclonal antibodies directed against proteins encoded by the above-mentioned DNAs, which are monospecific for mammalian, particularly human, Pc, and antibodies which are monospecific for JFBIg10 or JFSg2 encoded antigen(s) of mammalian Pc. This invention further encompasses reagents and compositions which include the above-mentioned DNAs, RNAs, proteins, chimeric molecules and monospecific antibodies, and methods of diagnosis, prophylaxis, and therapy in which the subject reagents and compositions are useful.

BRIEF DESCRIPTION OF FIGURES

FIG. 5 shows the nucleotide sequence of JFBIg10 DNA (Seq. ID #1) and the deduced amino acid sequence (Seq. ID #2) of the JFBIg10 protein product. The sequence of the homologous human Pc DNA from nucleotide 251 to 2814 is identical.

FIG. 6 shows in situ hybridization of lung tissue of Pc-infected rats with JBFIg10-derived RNA probes: Panel A shows hybridization with the antisense riboprobe as seen by light microscopy (left) and by reflected light image (right). Panel B shows results of hybridization of the same tissue sections with the sense riboprobe.

FIG. 8 shows the nucleotide sequence (Seq. ID #3) of JS7-2A3U DNA derived from rat Pc.

FIG. 9 shows the nucleotide sequence (Seq. ID #4) and restriction endonuclease sites of JFSIg2 DNA derived from rat Pc.

DETAILED DESCRIPTION OF INVENTION

Figure 1:
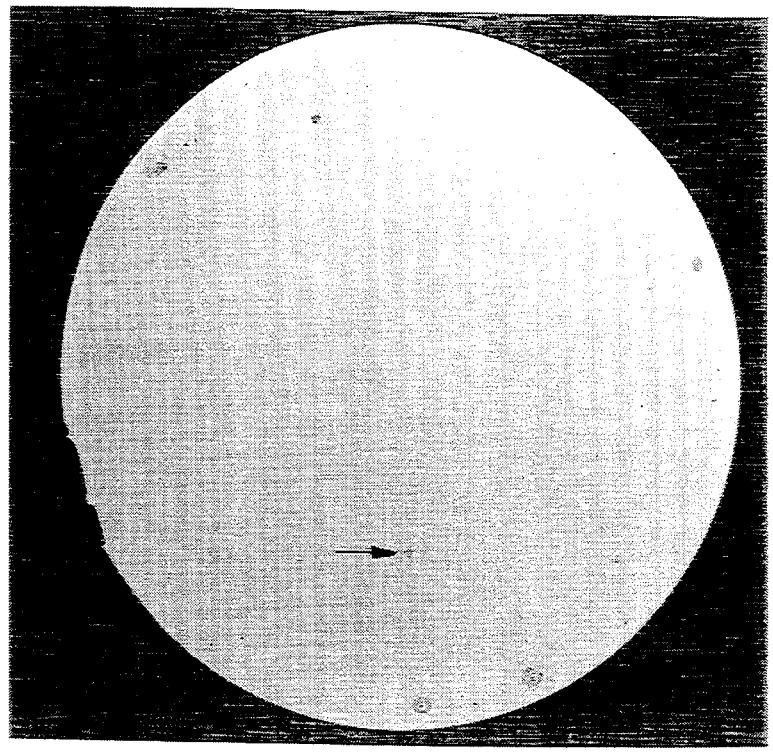
FIG. 1 shows a positive plaque detected on a plate of bacteriophage lambda gt11 containing the cDNA expression library derived from rat Pc screened with monoclonal antisera against gp116.

As described herein, DNA encoding antigens of mammalian Pc, referred to herein as JFBIg10 JFSg2 DNA, have been cloned and sequenced. The JFBIg10 protein product has been shown to be antigenically related to (i.e., to share epitopes with) a surface glycoprotein (or group of glycoproteins) of approximately 110–120 kD, referred to herein as gp116. gp116 is, both in terms of quantity and immunoreactivity, a major surface antigen found on both rat and human Pc. Thus, for the first time, the entire coding sequence of an immunologically significant antigen of mammalian Pc is available. As a result, as is also described herein, compositions and methods, such as probes, essentially pure proteins, vaccines, and methods of diagnosis, immunization, and prophylactic and therapeutic treatment of Pc infection and Pc pneumonitis (PCP), in which all or portions of the JFBIg10 DNA or an encoded product (e.g., RNA, proteins) are used, are also available.

As is also described herein, another DNA encoding a major surface antigen of rat Pc, designated JFSIg2 DNA, has been cloned and sequenced. Furthermore, DNA which is genetically related (or homologous) to JFBIg10 DNA, designated JS7-2A3U, has been cloned and sequenced.

The above-mentioned DNAs, as well as their encoded RNA and protein products, and compositions and methods using all or portions of these DNAs, RNAs, or proteins are described. Furthermore, chimeric molecules comprising all or a portion or portions of JFBIg10, JFSIg2, or JS7-2A3U DNAs, or all or a portion or portions of their encoded products are also included. This invention further provides antibodies, both polyclonal and monoclonal, which are monospecific for JFBIg10 or JFSIg2 encoded antigens(s) and antibodies which are monospecific for mammalian, particularly human, Pc, as well as chimeric molecules containing all or portions of these antibodies.

JFBIg10, JFSIg2, and JS7-2A3U DNAs, RNAs, proteins, chimeric molecules, and monospecific antibodies, and diagnostic, preventive and therapeutic compositions and methods using them are the subject of the present invention.

The following is a description of the cloning and characterization of JFBIg10 DNA of Pc obtained from rat lung (referred to as rat Pc), encoding a protein which is antigenically related to gp116, a quantitatively and immunologically major surface antigen found on both rat and human Pc; a comparison of the JFBIg10 gene and homologous DNA of Pc obtained from human samples (referred to as human Pc); a description of the cloning and sequencing of another DNA encoding a surface antigen of rat Pc; a description of the cloning and sequencing of DNA which is genetically related to JFBIg10 DNA; and a description of the above-mentioned DNAs, their RNA and protein products, related chimeric molecules and monospecific antibodies, and diagnostic, preventive and therapeutic compositions and methods in which they can be used.

Cloning and Characterization of JFBIg10 DNA from Rat Pc

Western analysis with polyclonal and monoclonal antisera against rat- and human-derived Pc detects a limited array of quantitatively major surface antigens (MsAgs) of Pc at approximately 111–120, 50–60, and 40–50 kilodaltons (kD). These antigens have both unique and shared epitopes and are found on Pc organisms derived from all mammalian host species. Additional unique antigens have also been identified. This invention is based on the cloning of DNA, designated JFBIg10 DNA, encoding a protein which cross-reacts with monoclonal antisera directed against a surface glycoprotein (or group of glycoproteins) of approximately 111–120 kD of Pc. This surface glycoprotein (or group of glycoproteins), referred to herein as gp116, is a quantitatively and immunoreactively major surface antigen found on both rat and human Pc. It is not known at present whether gp116 is a group of glycosylated variants of a single peptide, or whether gp116 is composed of a family of antigenically related glycosylated peptides, nor is it known how many genes encode the gp116 major surface antigen. It is reasonable to expect that JFBIg10 DNA encodes either the gp116 major surface antigen or a member of an antigenically related family of Pc surface antigens sharing epitopes with gp116.

In addition, as will be described further below, the JFBIg10 DNA from rat Pc has an identical homologous sequence in DNA from human Pc, indicating that the JFBIg10 protein product is an antigen found on Pc from at least two mammalian host species.

Thus, this invention describes for the first time the cloning of the entire nucleotide coding sequence (Seq. ID #1) and deduced peptide sequence (Seq. ID #2) of an immunologically significant antigen of Pc from a mammalian source, in particular, from rodent and human sources.

A number of reports have described the cloning of random pieces of the Pc genome, of genes encoding enzymes representing potential antibiotic targets in Pc, and of Pc ribosomal genes for diagnostic use. (Nakamura, Y. et al. (1989) *J. Protozool.* 36(1):58S–60S; WO 91/02092, J. S. Shah et al., Feb. 21, 1991)

In addition, some attempts to clone the gp116 major surface antigen gene have been reported. Smulian et al. reports the cloning of a cDNA, denoted PA 2, which encodes epitopes reacting weakly with anti-gp120 monoclonal antibodies (MAbs). (Smulian, A. G. (1991) Abstract WS7, *Program and Abstracts of the 44th Annual Meeting of the Society of Protozoologists, Jun. 28–Jul. 2,* 1991:47) Haidaris et al. reports the cloning of a portion of the gene encoding gp120 antigen of ferret Pc, and Nakamura et al. reports the cloning of cDNA encoding P115 antigen of rat Pc. None of the above reports the nucleotide or deduced amino acid (aa) sequences of their clones. Paulsrud et al. reports very limited aa sequence analysis of CNBr cleavage products of gp120. (Haidaris et al. (1991) Abstract WS4, *Program and Abstracts of the 44th Annual Meeting of the Society of Protozoologists, Jun. 28–Jul. 2,* 1991:46; Nakamura, Y. et al. (1991) Abstract WS6, *Program and Abstracts of the 44th Annual Meeting of the Society of Protozoologists, Jun. 28–Jul. 2,* 1991:46; Paulsrud, J. R. et al. (1991) Abstract WS2, *Program and Abstracts of the 44th Annual Meeting of the Society of Protozoologists, Jun. 28–Jul. 2,* 1991:46)

The following outlines the cloning and characterization of JFBIg10 cDNA from rat Pc. Pc were collected from steroid-treated, immunosuppressed rats and Pc RNA was extracted. A Pc cDNA expression library was constructed in bacteriophage lambda gt11. Approximately 120,000 amplified plaques were screened using monoclonal antisera directed against gp116 of rat Pc. The antisera (MAb5 and MAb6) have been previously described in Bogucki et al., which is hereby incorporated by reference. (Bogucki, M. S. et al. (1989) *J. Protozool.* 36(1):41S–43S) A positive clone was detected by screening with the antisera and subsequently purified through four rounds of rescreening (FIG. 1).

Figure 2A:
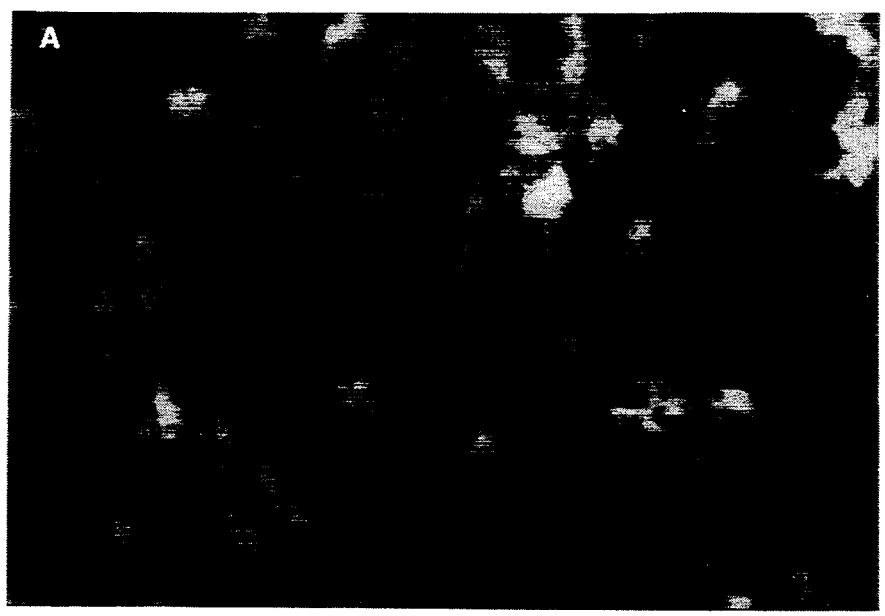
FIG. 2 shows immunofluorescent staining of rat- and human-derived Pc cysts and trophozoites with MAb6 antiserum: Panel A shows staining of cyst and trophozoites forms of rat Pc. Panel B shows staining of Pc cysts from a bronchoalveolar lavage specimen from a patient. Panel C shows staining of Pc in paraffin tissue sections from human lung.
Figure 2B:
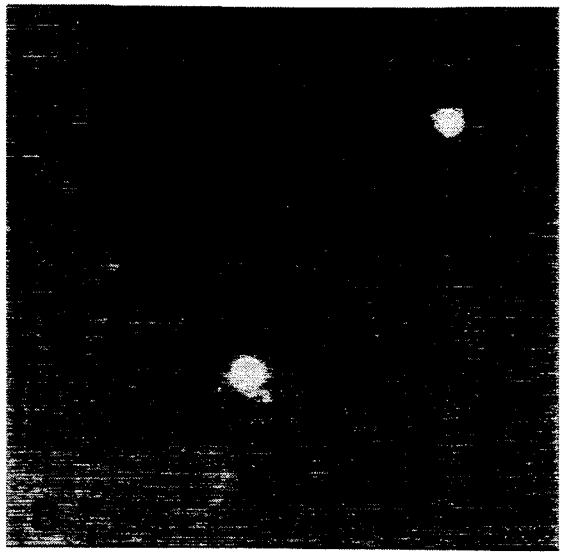
Figure 2C:
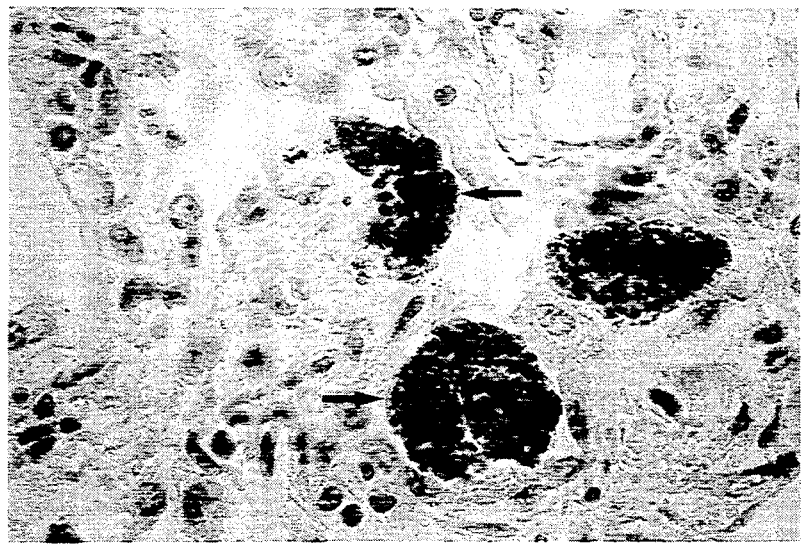
Figure 3:
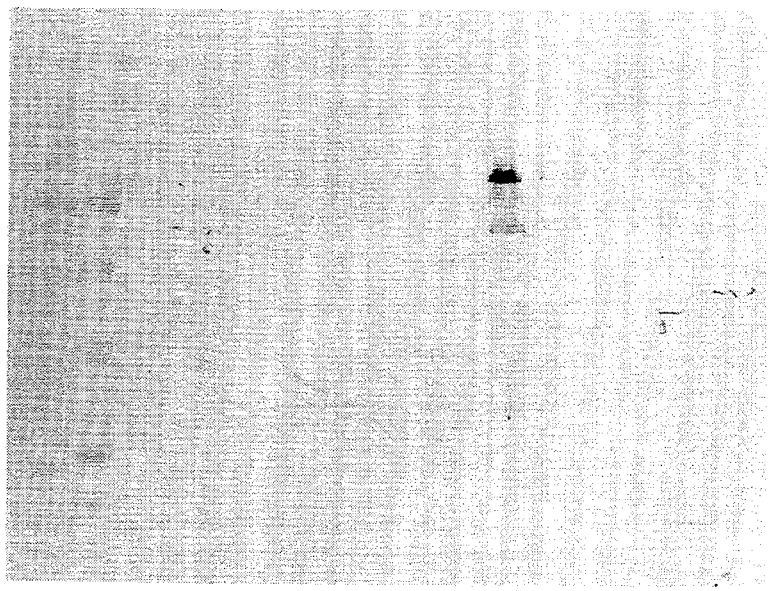
FIG. 3 shows a Western blot of fusion proteins expressed by clones from the rat Pc cDNA expression library screened with MAb6 antiserum: Lanes A and B contain protein expressed by random clones from the cDNA expression library. Lanes C and D contain protein expressed by the JFBIg10 clone at two dilutions. Lanes E and F contain protein expressed by clones of lambda gt11 bacteriophage without cDNA insert. Molecular weight standards (MW) indicate that the primary reaction product is over 214 kD in molecular weight.

The purified clone, designated the JFBIg10 clone, was expressed as a β-galactosidase fusion peptide from lambda recombinant lysogens in *E. coli* Y1089 and probed on Western immunoblots with the MAb6 monoclonal antibody, which recognizes gp116 of both rat- and human-derived Pc (FIG. 2). The JFBIg10 protein product was immunoreactive with MAb6, indicating that it shares epitopes with the gp116 major surface antigen of rat and human Pc (FIG. 3). Molecular weight standards indicate that the primary reaction product is a fusion protein of over 214 kD in molecular weight.

Figure 4:
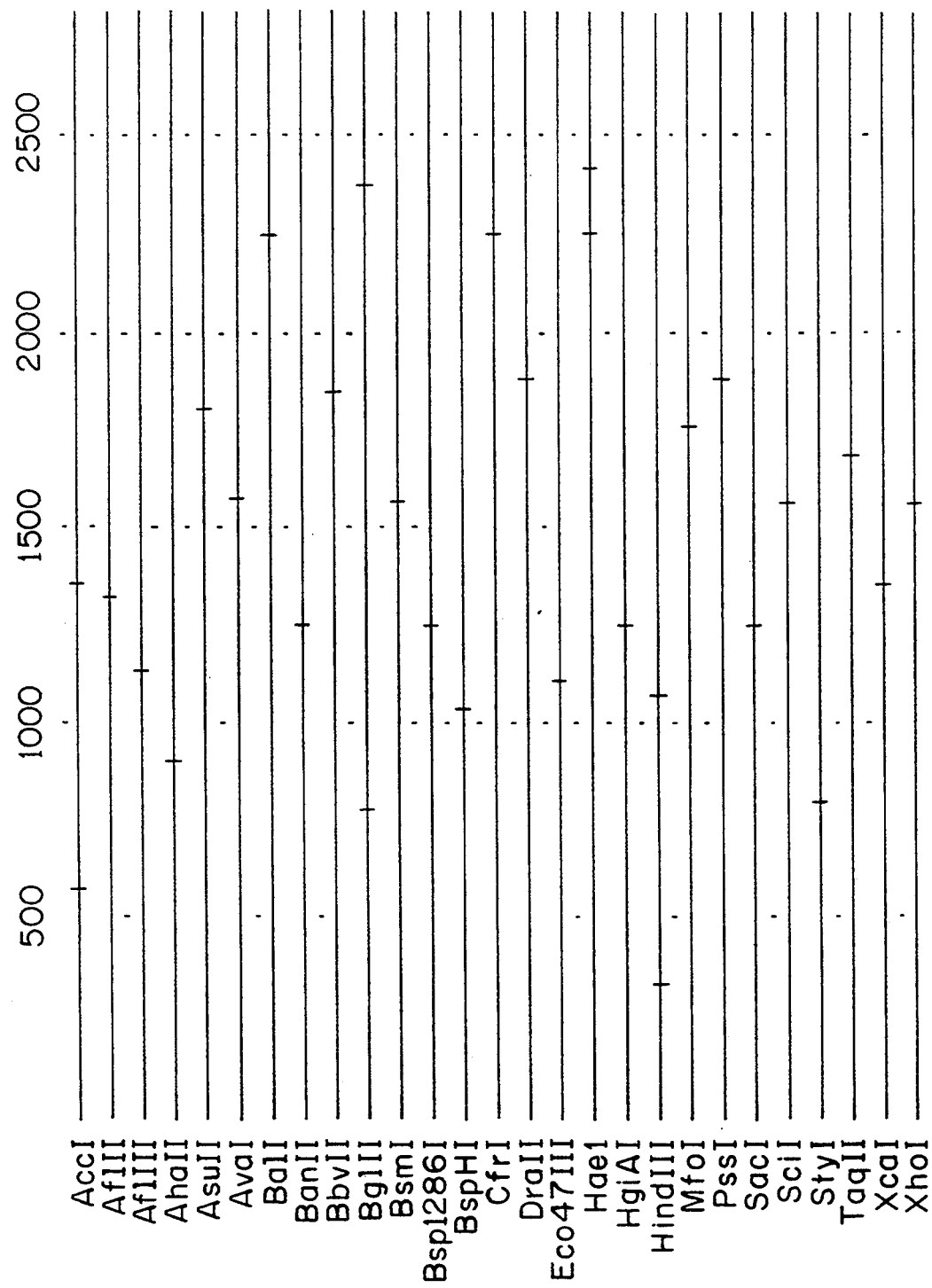
FIG. 4 shows a restriction endonuclease site map of the JFBIg10 cDNA insert.

Restriction endonuclease site analysis was performed on the JFBIg10 DNA insert (FIG. 4). An EcoR1 fragment of the JFBIg10 cDNA insert was subcloned into pUC18, followed by sequencing of both strands of the DNA using a combination of primer walk and Exo/Mung deletion strategies. The entire sequence was checked by polymerase chain reaction (PCR) amplification of segments of the DNA with subsequent sequencing. Sequence information was assembled using sequence analysis software of the Genetics Computer Group, University of Wisconsin. The nucleotide sequence of JFBIg10 DNA (Seq. ID #1) and the deduced amino acid sequence (Seq. ID #2) of the translation product are shown in FIG. 5.

The JFBIg10 DNA was also subcloned into pGEM3Z (Promega Scientific) and used to make $^{35}$S-labelled sense and antisense RNA probes. The riboprobes were used to detect Pc in lung tissues from Pc-infected and uninfected rats by in situ hybridization, as well as to Northern blots of RNA from Pc-infected and uninfected animals. Northern blots revealed a quantitative relationship between intensity of the hybridization signal to the antisense riboprobe and the amount of Pc in a given lung specimen used to make the RNAs. DNA and RNA probes derived from JFBIg10 DNA reacted with material from infected rat lungs and did not react with material from uninfected rat lungs when tested in twelve infected and nine uninfected animals. In situ hybridization also showed hybridization of the antisense riboprobe to infected tissue (FIG. 6). No hybridization of the sense riboprobe or to uninfected tissue was observed. These results indicate that JFBIg10 is of Pc and not mammalian host origin.

Figure 7:
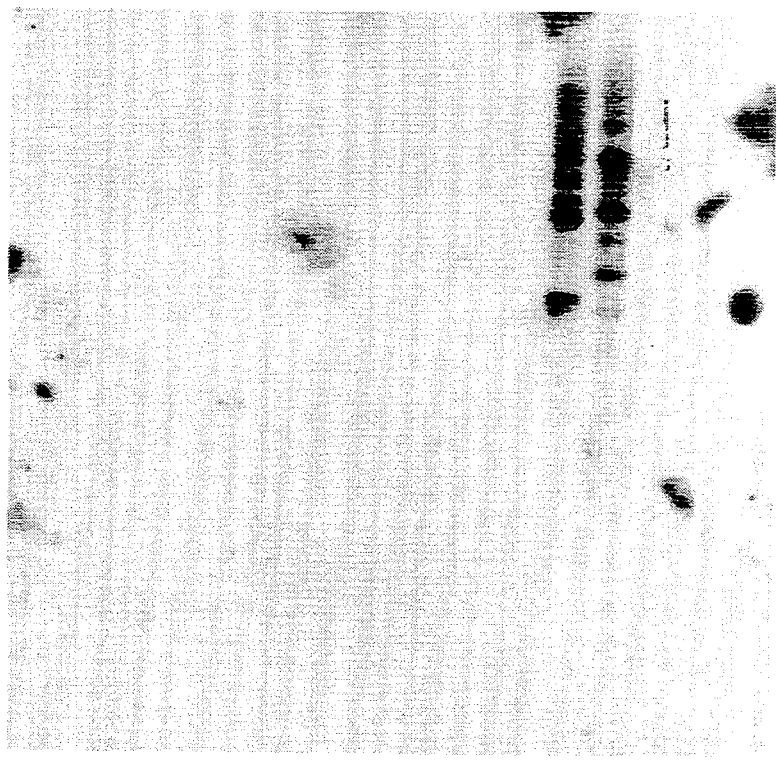
FIG. 7 shows a Southern blot of genomic DNAs cut with EcoR1 and Sac1 from lambda bacteriophage (A, P); human (B, C); lambda gt11 (D, E); E. coli (F, G); mink cells (CCL-64, H, I); rat (J, K); and S. cerevisiae. Lanes L and M show P. carinii DNA cut with EcoR1 (L) and Sac1 (M), respectively.

The Pc origin of JFBIg10 DNA was further demonstrated by a hybridization experiment using JFBIg10 DNA to probe a Southern blot of genomic DNAs from a variety of potential contaminating organisms. The hybridization results showed binding only to DNA from Pc and not to DNAs from yeast, human, *E. coli*, bacteriophage lambda gt11, mink, or rat (FIG. 7).

Analysis of the nucleotide sequence of the JFBIg10 DNA insert (Seq. ID #1) reveals a 2814 bp cDNA containing an 1197 bp open reading frame in a single orientation with a possible polyadenylation signal and polyA tract in terminal locations. The deduced aa sequence (Seq. ID #2) indicates a peptide of 399 aa residues. Given an average molecular weight of 110 for each amino acid, the deduced amino acid sequence would then encode an unglycosylated peptide of about 44 kD.

Comparison of the nucleotide sequence or the deduced peptide sequence of the 2814 bp DNA insert with GenBank and Swissprot databases using either the BlastX protocol (NIH) or the Wisconsin Wordsearch protocol (GCG) showed no significant homology to published sequences. The highest level of similarity observed is of a short segment of the nucleotide sequence to *Dictyostelium discoideum* (slime mold) cDNA for the phosphodiesterase gene. Amino acid sequence similarity of 12 aa was detected to a short region of the gp160 precursor of Human Immunodeficiency Virus-1 (HIV-1).

Relatedness of Rat and Human Pc JFBIg10 DNA

Concerns about the relatedness of the Pc organisms derived from clinical (human) samples and from rat-derived Pc were addressed using polymerase chain reaction (PCR) amplification of human sequences using primers derived from the JFBIg10 rat Pc sequence. The sequence of the human Pc gene was identical to that of the rat Pc gene over the entire 2756 bp (including the open reading frame) for which high Tm primers could be synthesized. Each of the pairs of PCR primers was used to amplify segments from at least two different patient DNA samples with two negative human samples as simultaneous controls. No differences have been detected to date using multiple human hosts as sources for the material probed. The human Pc sequence is shown between nucleotides 251 and 2814 of the nucleotide sequence in FIG. 5.

Cloning and Characterization of Genetically Related Nucleotide Sequences

Hybridization of a JFBIg10 DNA probe to rat Pc DNA indicates that the JFBIg10 gene is a member of a family of homologous nucleotide sequences in the Pc genome (FIG. 7, Lanes L and M). This is indicated by the multiple sizes of EcoR1 and Sac1 fragments containing sequences hybridizing specifically to a JFBIg10 DNA probe under stringent hybridization conditions (as indicated by the lack of hybridization to non-Pc DNAs). The JFBIg10 DNA has only a single EcoR1 site and a single Sac1 site (FIG. 4) and can account for, at most, two of the hybridizing bands in each lane. These genetically related DNAs can be cloned by screening mammalian Pc DNA fragments with a JFBIg10 DNA or RNA probe, as will be described further below.

One homologous sequence of JFBIg10 DNA, designated JS7-2A3U DNA, was cloned and sequenced. Its nucleotide sequence (Seq. ID #3) is similar to, but distinct from the JFBIg10 sequence. The JS7-2A3U DNA insert is 1448 bp long. The first 1056 bp (from the 5' end of the insert) of the JS7-2A3U sequence is similar to the JFBIg10 sequence, with 55 single bp differences. The remaining sequence after nucleotide 1056 diverges significantly from the JFBIg10 sequence. The nucleotide sequence of JS7-2A3U is shown in FIG. 8.

Cloning of JFSIg2, Another DNA Encoding a Pc Surface Antigen

As discussed above, the molecular nature of the Pc surface antigen is not well understood. The isolation and analysis of DNAs encoding these antigens, should help to clarify the structure and processing of the antigens, their function in Pc biology, and their role in immunologic interactions between Pc organisms and mammalian hosts. DNAs encoding Pc surface antigens may be obtained by cloning and screening methods similar to those described above, which resulted in the cloning of the JFBIg10 gene.

This is demonstrated by the cloning of another cDNA derived from rat Pc, referred to herein as JFSIg2 DNA, whose encoded peptide product also cross-reacts with monoclonal antibodies directed against rat Pc. The nucleotide sequence of JFSIg2 (Seq. ID #4) is shown in FIG. 9.

JFBIg10, JS7-2A3U, and JFSIg2 DNA and Products Derived Therefrom

This invention claims DNA comprising all or a portion or portions of the nucleotide sequences of JFBIg10 DNA (FIG. 5), (Seq. ID #1) JS7-2A3U DNA (FIG. 8 (Seq. ID #3)), and JFSIg2 DNA (FIG. 9 (Seq. ID #4)), as well as the RNAs and protein products encoded by this DNA. The protein products may be glycosylated or unglycosylated peptides. In particular, antigens of mammalian Pc as encoded by JFBIg10 and JFSIg2 are the subject matter of this invention. This invention also includes functional equivalents of the afore-mentioned DNA, RNA, or proteins. A functional equivalent of a nucleic acid sequence is a nucleotide sequence which, through the degeneracy of the genetic code, encodes the same peptide gene product as the original. A functional equivalent of a nucleic acid or protein may also contain a modification of the molecule such that the resulting gene product is similar enough to that encoded by the unmodified sequence that it has essentially the same activity. An example of such a modification would be a "silent" codon or aa substitution, for instance, from one acidic aa to another, or from one codon encoding a hydrophobic aa to another codon encoding a hydrophobic aa. The above-claimed DNA, RNA, and proteins refer to substantially pure or isolated nucleic acids and proteins, which are obtained by isolation from natural sources, by genetic engineering, or by chemical synthesis.

In addition, the DNA claimed includes expression vectors comprising all or portions of the nucleotide sequences shown in FIGS. 5 (Seq. ID #1, 3, 4), 8, and 9. The expression vectors include vectors which allow expression of antisense RNA complementary (that is, capable of specific hybridization) to the coding sequence of the translated product of the DNA. Several expression vector/host systems are available commercially or can be reproduced according to recombinant DNA and cell culture techniques. The vector/host expression systems may be prokaryotic or eucaryotic. They may be systems which process and glycosylate the translated product encoded by the nucleotide sequence in an appropriate host, such as the yeast or vaccinia virus expression systems. The vectors may contain signals for secretion of the encoded protein from the host. In addition, the expression vectors may be virus vectors, which allow expression of the encoded protein or antisense RNA in humans. The construction of expression vectors and transfer of the vectors into various host cells can be accomplished using genetic engineering techniques, as described in manuals like *Molecular Cloning* and *Current Protocols in Molecular Biology*, which are hereby incorporated by reference, or by using commercially available kits. (Sambrook, J., Fritsch, E. F., and Maniatis, T., *Molecular Cloning*, 2nd Edition, Cold Spring Harbor Press, 1989; Ausubel, F. M. et al., *Current Protocols in Molecular Biology*, Greene Publishing Associates and Wiley-Interscience, 1988).

Monoclonal and polyclonal antibody preparations directed against JFBIg10 and JFSIg2 encoded antigens are also within the scope of this invention. The antibody preparations comprise antibodies which are monospecific for mammalian, particularly human, Pc, and which do not cross-react with mammalian antigens, and to antibodies which are monospecific for the encoded antigens of mammalian Pc, and which do not cross-react with host or other Pc antigens. The monospecific antibodies also include antibodies which are able to distinguish Pc antigen(s) related to AIDS from non-AIDS-related Pc antigens, and PCP-related antigen(s) of Pc from non-PCP-related Pc antigen(s). The monospecific antibody preparations can be obtained using the encoded antigens of this invention for immunization and screening of antisera, according to immunization and recombinant DNA procedures described in the following publications, which are incorporated by reference. (Harlow, E. and Lane, D., *Antibodies: A Laboratory Manual*, Cold Spring Harbor Laboratory Press, 1988; Huse, W. D. et al. (1989) *Science* 246:1275–1281; Moore, G. P. (1989) *Clin. Chem.* 35(9):1849–1853) The antigens used to obtain the antibody preparations may be unglycosylated peptides or glycoproteins. Glycosylated antigens encoded by JFBIg10 and JFSIg2 DNA sequences can be produced in an appropriate expression system, as discussed above.

In addition, this invention includes chimeric molecules consisting of a protein moiety A encoded by all or a portion of the JFBIg10, JS7-2A3U, and JFSIg2 nucleotide sequences (Seq. ID #1, 3, and 4) in conjunction with a moiety B, which may be a detectable marker, an antifungal toxin, or an antibody. Also included are chimeric molecules composed of a moiety A, which is a monospecific antibody described above, or an immunoreactive portion of the antibody, and a moiety B, which can be a detectable label, an antifungal toxin, or another antibody. Expression vectors encoding such chimeric molecules are also included. Chimeric nucleic acids and proteins can be constructed using recombinant DNA techniques. Chimeric antibody molecules can also constructed by recombinant DNA, as well as by other techniques. (Waldmann, T. A. (1991) *Science* 252:1657–1662)

Other surface antigens of mammalian-derived Pc and DNAs encoding these antigens can be obtained by the method described for cloning JFBIg10 and JFSIg2 DNAs, that is, by screening an expression library of Pc cDNA with antisera directed against mammalian Pc.

Diagnostic and Therapeutic Applications

The DNAs, RNAs, proteins, and related products (e.g., antibodies, chimeric molecules) described above have many diagnostic, prophylactic, and therapeutic uses, as described below.

Probes and Diagnostic Methods

Reliable, quick, and sensitive quantitative diagnostic assays for human Pc are essential for epidemiologic studies of PCP and non-invasive early diagnosis of PCP in patients. Of particular clinical interest is the application of methods for detection and quantitation of human Pc in samples not requiring invasive methods of collection, such as sputum samples. (Kovacs, J. A. et al. (1988) *New England J. Med.* 318(10):589–593) Diagnosis of Pc infection in its early stages requires adequate sensitivity of the diagnostic method to detect the low concentrations of Pc organisms in the sample. In addition, the diagnostic method used should be specific for Pc or a Pc component(s), due to the complex composition of the sample. For example, in sputum samples of AIDS patients, Candida yeast infection of the oral cavity can be a complicating factor.

Diagnostic methods are available which employ Pc-specific nucleic acid probes for ribosomal RNA or DNA of Pc. (WO 91/02092, J. S. Shah et al., Feb. 21, 1991) DNA and RNA probes for mammalian, particularly human, Pc can be derived from the JFBIg10, JS7-2A3U, and JFSIg2 nucleotide sequences shown in FIGS. 5, 8, and 9, (Seq. ID #1, 3, and 4) respectively. A probe can contain all of the nucleotide sequence, or a portion of the nucleotide sequence which is capable of specific hybridization to a nucleotide sequence characteristic of Pc. An RNA or riboprobe can be derived from either the sense or antisense strand of the nucleotide sequence, if used to probe double-stranded DNA. However, only the antisense RNA probe should be used to detect single-stranded DNA or RNA samples. DNA and RNA probes can be labelled by a number of standard techniques, as described in manuals like the above-referenced *Molecular Cloning* or *Current Protocols in Molecular Biology*, or by commercial kits.

Probes can also be derived from the above-mentioned nucleotide sequences for use as primers in polymerase chain reaction (PCR) amplification of homologous or identical nucleotide sequences. PCR amplification of a segment of a nucleotide sequence requires sets of primers which hybridize both 5' and 3' to the amplified sequence. The set of PCR primers may be nested in order to confirm the amplified sequence.

The above-described DNA, RNA, and PCR probes can be used for detection and quantitation of mammalian Pc. Of particular clinical interest would be diagnostic assays for human Pc. One embodiment of a method of detecting mammalian Pc in a sample includes the following steps: 1) treating the sample to render nucleic acid in the sample available for hybridization to a probe; 2) performing a hybridization reaction under conditions appropriate for specific hybridization of a labelled probe derived from the nucleotide sequence of JFBIg10 DNA (as shown in FIG. 5 (Seq. ID #1) to complementary sequences in the nucleic acid in the sample; and 3) detecting hybridization in the hybridization reaction, wherein specific hybridization indicates the presence of mammalian Pc in the sample. The conditions of the hybridization reaction, including temperature, salt concentration of hybridization medium, and concentration of probe and sample, can be adjusted to obtain specific hybridization of the probe. For example, the conditions may be less stringent when using a probe derived from human Pc to detect mouse Pc than to detect human Pc. The adjustment of hybridization conditions, as well as techniques for performing the basic steps described above, are known and are also described in the above-referenced manuals.

Figure 10:
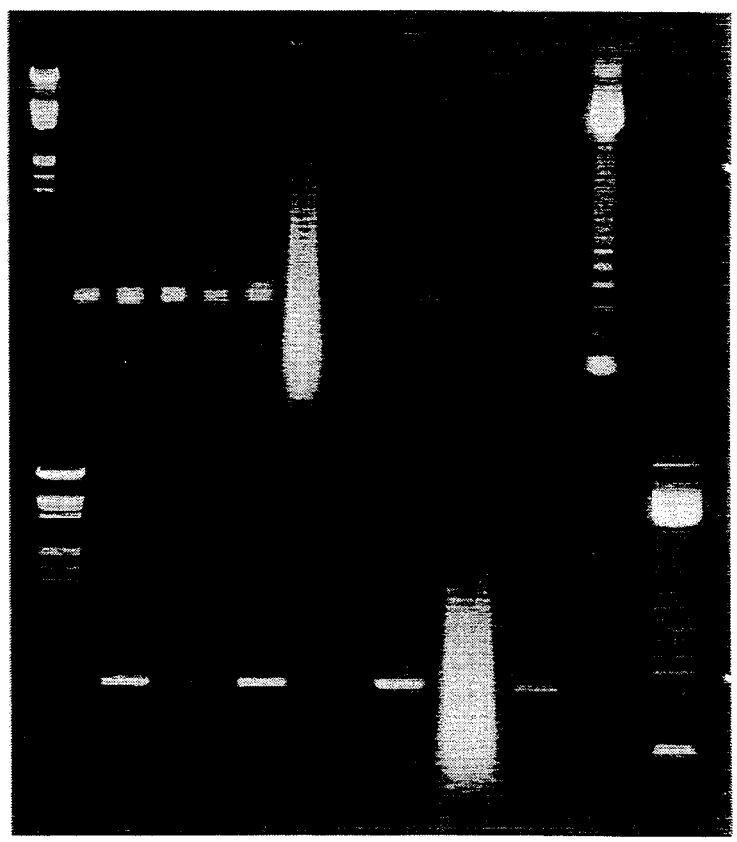
FIG. 10 shows PCR amplification of genomic DNA from rat and human Pc using primers derived from JFBIg10 DNA. Control preparations are seen in Lanes 7, 8, 9, and 10 in the top for rat genomic DNA and in Lanes 4 and 8 at the bottom for human genomic DNA. Specific amplified bands of rat Pc DNA are seen in Lanes 1, 2, 3, 4, 5, and 9 on the top. Specific amplified bands of human Pc DNA are seen in Lanes 1, 2, 3, 5, and 7 on the bottom. Size markers are present on the extreme left and right lanes.

One embodiment of a method of detecting mammalian Pc using PCR probes includes the following steps: 1) rendering nucleic acid in the sample available for PCR amplification; 2) performing PCR amplification of the nucleic acid under conditions appropriate for specific amplification of nucleotide sequences which hybridize to a set of primers derived from the nucleotide sequence of JFBIg10 (as shown in FIG. 5 (Seq. ID #1); and 3) detecting specific amplification, wherein occurrence of specific amplification indicates the presence of mammalian Pc in the sample. Specific amplification can be confirmed by sequencing the amplified DNA or by using nested PCR primers to amplify internal segments of the amplified sequence. FIG. 10 illustrates the use of PCR primers with human and rat genomic DNAs. Specific amplified bands are seen in Lanes 1, 2, 3, 4, 5, and 9 on the top and 1, 2, 3, 5, and 7 on the bottom.

A clinical diagnostic application of the PCR detection method is the detection of Pc or Pc nucleic acids in human blood samples. Due to pulmonary injury during pneumonia, some Pc or Pc nucleic acids may "leak"

into the circulation allowing PCR detection. Detection of Pc nucleic acids in blood samples from Pc-infected patients has been demonstrated with PCR primers derived from the JFBIg10 nucleotide sequence (Seq. ID #1).

An epidemiologic application of the PCR detection method is for detection of putative multiple "strains" of Pc in Pc-infected patients. Correlation of strain differences to geographic location may indicate a common source outbreak of Pc infection. Multiple strains of Pc can be identified by 1) PCR amplification of homologous nucleotide sequences in the Pc nucleic acids from different samples, that is, amplification from the same set of primers; 2) sequencing the homologous amplified DNAs from the different samples; and 3) comparing the homologous sequences from the different samples, wherein differences of the homologous nucleotide sequences in Pc from different samples indicates multiple strains of Pc.

PCR amplification can also be used to obtain nucleotide sequences which are homologous to a nucleotide sequence from which PCR probes are derived. One embodiment of this method is a method for obtaining homologous nucleotide sequences to the JFBIg10 DNA sequence, (Seq. ID #1) and includes the following steps: 1) performing PCR amplification on mammalian Pc nucleic acid, under conditions suitable for specific amplification of nucleotide sequences which hybridize to a set of primers derived from the nucleotide sequence (Seq. ID #1) of JFBIg10 DNA (as shown in FIG. 5), thereby producing amplified DNA containing the homologous sequence; 2) cloning the amplified DNA, or portion containing the homologous sequence; and 3) sequencing the cloned DNA.

Quantitative immunoassays for clinical use have not been readily available due to lack of antibody preparations which are monospecific for human Pc antigens (as distinguished from host or other Pc antigens). This problem is due to the fact that Pc antigens share a number of epitopes with mammalian host cells, with Pc from various mammalian species (for example, rat, ferret, mouse, and human) and with other Pc antigens. However, Pc antigens also have unique epitopes, supporting the possibility that monospecific antibody preparations are obtainable. Monospecific antisera are critical for quantitative immunoassays which do not require a separation or extraction step for the Pc component being measured, such as in Western blotting. Thus, monospecific antibody preparations are necessary to the availability of commercially viable and clinically useful immunoassays. (Graves, D. C. (1989) *J. Protozoology* 36(1):60–69; Kovacs, J. A. et al. (1988) *J. Immunol.* 140(6):2023–2031; Gigliotti, F. (1991) Abstract WS5, *Program and Abstracts of the 44th Annual Meeting of the Society of Protozoologists, Jun. 28–Jul. 2, 1991*:46; Bogucki, M. S. et al. (1989) *J. Protozool.* 36(1):41S-43S).

The potential utility of quantitative immunoassays for human Pc is illustrated by Walzer et al., which shows by Western blotting technique that Pc from AIDS patients with PCP had significantly stronger immunoreactivity to anti-Pc antisera than Pc from non-AIDS patients with PCP. Speculative explanations include higher Pc burden of AIDS over non-AIDS patients and antigenic variation between AIDS and non-AIDS Pc. This and other studies suggest the need for quantitative assays and specific immunodiagnostic probes for Pc antigens due to the high rate of anti-Pc antibodies in the healthy human population. (Walzer, P. D. et al. (1987) *J. Immunol.* 138(7):2257–2265; Levin, M. R. (1983) *Am. Rev. Resp. Dis.* 128:182)

Linder et al. reports a Pc-specific Mab, 2E3, which reacts with an 82 kD surface antigen of human Pc, and does not cross-react with human lung or various rat tissues or with a number of other parasites and fungi. Antiserum specific for a Pc cell wall component has also been reported. (Linder, E. et al. (1987) *J. Immunolo. Methods.* 98:57–62; Matsumoto, Y. et al. (1987) *Parasitol. Res.* 73:228–233)

The monospecific antibodies and chimeric molecules containing all or immunoreactive portions of the monospecific antibodies described above can be used as immunoreactive probes, that is, probes which detect antigens by specific antibody-antigen binding. One embodiment of a method of detecting mammalian Pc in a sample using an immunoreactive probe of this invention includes the following steps: 1) reacting the sample with an immunoreactive probe comprising either all or an immunoreactive portion of an antibody directed against the JFBIg10 encoded antigen, or a chimeric molecule consisting of the antibody or antibody portion and a detectable label, the immunoreactive probe being monospecific for mammalian Pc, under conditions suitable for specific binding of the probe to antigens in the sample; and 2) detection of specific binding in Step 1), where occurrence of specific binding indicates the presence of mammalian Pc. A method for detection of the JFBIg10 antigen of mammalian Pc follows the same steps, except that antibodies or chimeric molecules which are monospecific for the JFBIg10 antigen and not for other Pc or host antigens are used as the immunoreactive probe.

A method for quantitation of mammalian, particularly human, Pc or for quantitation of an antigen of mammalian Pc, also follows basically the same steps, except that, instead of detection in Step 2), measurement of the extent of specific binding between the immunoreactive probe and the antigen in the sample is determined, where the extent of probe-antigen binding is indicative of the amount of Pc or antigen in the sample. Immunoreactive probes for mammalian Pc and for JFSIg2 Pc antigen can also be used in the above methods. Techniques for performing Steps 1 and 2 and for adjustment of the conditions for specific binding of the immunoreactive probe to the desired antigen(s) in the immunodiagnostic methods described above are known and are also described in the above-referenced *Antibodies: A Laboratory Manual* and *Current Protocols in Molecular Biology*.

Vaccine compositions and immunization against Pc infection and PCP:

Data on the successful vaccination of AIDS patients against common infections (egs. DPT, hepatitis B, pneumococcus, HiB) support the potential utility of a recombinant Pc antigen vaccine in the prevention of PCP for a variety of immune deficiencies. Indeed, the rat Pc antigen P115 has been shown to be strongly antigenic to sera from humans with diagnosed PCP. (Nakamura, Y. et al. (1989) *J. Protozool.* 36(1):58S–60S) Furthermore, passive immunization with a monoclonal antibody directed against a surface antigen shared by the Pc of several mammals has been shown to confer partial protection against PCP in animal models. This indicates the potential for passive immunization against PCP and the need for stronger neutralizing anti-Pc antibodies. Recent studies suggest that enhancement of the humoral and mucosal, as well as cell-mediated, immune systems could significantly improve prognosis of patients at risk for Pc infection and PCP. (Gigliotti, F. and Hughes, W. T. (1988) *J. Clin. Invest.* 81(6):1666–8; Hofmann, B. et al. (1985) *J. of Infect. Dis.* 152(4):838–840)

Vaccine compositions for active or passive immunization against Pc infection and PCP can be prepared, which comprise all or immunogenic portions of the encoded antigens of JFBIg10 (Seq. ID #1) and JFSIg2 (Seq. ID #4) nucleotide sequences; expression vectors encoding all or portions of these antigens; antibody preparations specific for mammalian, particularly human, Pc; and chimeric molecules containing a moiety A, which consists of all or active portions of these antigens and antibodies. The chimeric molecule may carry a second moiety B, which increases protective effectiveness of the vaccine. Expression vectors may be delivered via infection with recombinant virus, for example, by recombinant retrovirus or, preferably, by recombinant adenovirus vaccine.

Anti-*P. carinii* Agents:

Pc is an extracellular fungus which binds tightly to type I alveolar epithelial cells. The determinants and function of this interaction are unknown. Probably as a result of this binding, injury to and sloughing of the type I cells occurs with proliferation of the type II epithelial cells. Recently, the gp120 surface antigen of Pc has been implicated in the binding of Pc to host cells. Anti-gp120 antibodies and small quantities of gp120 peptides have been reported to inhibit the attachment of Pc to and growth of Pc on cultured cells, suggesting the potential for clinical treatment of Pc infection and PCP using substantially pure surface antigens and anti-surface antigen antibodies as anti-fungal agents which interfere with the binding of Pc to host cells. (Paulsrud, J. R. et al. (1991) Abstract WS2, *Program and Abstracts of the 44th Annual Meeting of the Society of Protozoologists,* Jun. 28–Jul. 2, 1991:46; Pottratz, S. T. et al. (1990) *Clin. Res.* 38(2):466A; Pottratz, S. T. et al. (1990) *Am. Rev. Resp. Dis.* 141:A271)

However, methods of obtaining uncontaminated, intact surface antigens from natural sources have been unreliable. The range and pattern of sizes of rat and human Pc antigens in general have been observed to be affected by the method of isolation and host of origin of Pc and by experimental conditions and antisera used to detect the antigens. It is conjectured that heterogeneity of the gp116 surface antigen of Pc may be attributable to variation in the carbohydrate chains of the glycoprotein, while the peptide backbone is essentially unchanged. The functional and structural relationships between the variant forms of gp116 from different mammalian sources of Pc and even within a preparation of Pc remain to be elucidated. (Nakamura, Y. et al. (1989) *J. Protozool.* 36(1);58S–60S; Gigliotti, F. (1991) Abstract WS5, *Program and Abstracts of the 44th Annual Meeting of the Society of Protozoologists,* Jun. 28–Jul. 2, 1991:46; Kovacs, J. A. et al. (1988) *N. E. J. Med.* 318:589–593; Walzer, P. D. and Linke, M. J. (1987) *J. Immunol.* 128:2257–2265; Graves, D. C. et al. (1986) *Infect. Immun.* 54:96–103; Maddison, S. E. et al (1982) 15:1036–1043) As a consequence, uncontaminated preparations of intact gp116 glycoprotein(s) for prophylactic and therapeutic use have not been available.

This invention provides a means to produce essentially pure proteins which are either gp116 or other Pc antigens or for therapeutic and prophylactic use in anti-Pc compositions by recombinant DNA techniques or peptide synthesis based on the JFBIg10 and JFSIg2 DNA and the deduced amino acid sequences of their encoded protein products. In addition, expression vectors encoding the antigens can be administered through viral infection, as discussed above, for production of the proteins in mammalian host cells.

Furthermore, monospecific antibodies, as discussed above, may be used as anti-Pc agents for preventive and/or therapeutic treatment of Pc infection and PCP. Chimeric molecules comprising a portion of an anti-Pc antibody sufficient to bind specifically to Pc can be used to target antifungal toxins or anti-Pc neutralizing antibodies to Pc organisms.

In addition, anti-Pc agents comprising antisense RNA and expression vectors encoding antisense RNA derived from the JFSIg10 and JFSIg2 nucleotide sequences can be prepared according to this invention. Antisense RNA may be used to interfere with gp116 or antigenically related protein expression by Pc cells and thus, with Pc binding to host cells.

EXAMPLES

1. Collection of rat Pc, rat Pc DNA and rat Pc RNA

*Pneumocystis carinii* were derived from steroid-treated, immunosuppressed rats using the transtracheal inoculation method described by Fishman and Bartlett et al., which are incorporated by reference. (Fishman, J. A. (1987) *Amer. Fed. Clin. Res.* 36:455A; Bartlett, M. S., et al. (1988) *J. Clin. Microbiol.* 26:1100–1102) In brief: Sprague Dawley rats (Harlan Sprague Dawley, Indianapolis, pathogen-free, barrier raised) are fed water containing dexamethasone (1 mg/l) and tetracycline (500 mg/l) ad libitum. They also receive a normocaloric, low (8%) protein rat diet (ICN Pharmaceuticals). After 5–7 days on this regimen, the rats are inoculated intratracheally with $10^6$ to $10^7$ Pc (including up to 10% cyst forms on Giemsa-stained smears) derived from prior infections. Lungs are harvested under sterile conditions after 6 to 12 weeks. Impression smears are taken from the cut surface of each lung, the lung cultured for bacteria and fungi, and individually chopped and homogenized in a Stomacher apparatus (Tekmar Inc., Cincinnati, Ohio). The homogenate is centrifuged and the supernatant diluted to 40 ml with DMEM with antibiotics. The supernatant is serially filtered through Nucleopore filters of 10, 8, 5 (twice) microns and the Pc collected by centrifugation for 15 minutes at 4000 rpm. Smears of 10 ul of resuspended organisms are spread over a 1 $cm^2$ premarked slide and stained with DiffQuik for counting of Pc nuclei and host cells. No intact nucleated cells are present after filtration. Red cells are lysed with ammonium chloride buffer, the pellet rewashed and resuspended in a desired medium.

Pc DNA is collected using organisms treated for 15 minutes at 37° C. with a solution of Zymolyase 100T (Seikagaku America, Rockville, Md., 400 U/ml) in 50 mM TrisCl, 10 mM $MgCl_2$, 1M sorbitol, and 1 mM DTT. Lysis is performed by a modification of the method in *Current Protocols in Molecular Biology* (Ausubel et al., pp. 13.13.4–13.13.7). Nitric acid washed glass beads (400 mg, Sigma, 425–600 micron) are vortexed (2×1 minutes) with phenol (equilibrated with lysis buffer) and 500 ul of Pc solution. This mixture is centifuged to remove the beads, extracted twice with chloroform:isoamyl alcohol (24:1), ethanol precipitated twice, and dialyzed against 0.1M TrisCl, pH 8.0 for 6 hours. The resulting nucleic acids (DNA and RNA) are reprecipitated for use.

Pc RNA was extracted according to the Guanidinium Extraction Method published in *Molecular Cloning*, size-fractionated, blunt-ended and linkered with EcoR1 linkers.

2. Cloning and Characterization of JFBIg10 cDNA

An expression library of cDNA derived from rat Pc in bacteriophage lambda gt11 was a gift from Dr. E. Ullu, Yale University School of Medicine. Monoclonal antisera (MAb5 and MAb6) directed against the gp116 of rat Pc were a gift from Dr. F. Richard, Yale University School of Medicine. MAb5 and MAb6 have been previously described in Bogucki et al., which is incorporated herein by reference. (Bogucki, M. S. et al. (1989) *J. Protozoology* 36:41–44S)

Approximately 120,000 amplified plaques were screened using MAb5 and MAb6 monoclonal antisera directed against the gp116 major surface antigen of rat Pc. Immunofluorescent staining of rat and of human-derived Pc was performed using 1:20 and 1:100 dilutions of the antisera in phosphate buffered saline (PBS) and affinity purified goat anti-mouse fluorescein labelled second antibody (Cappel Labs, Malvern, Pa.). Each antiserum was also tested against rat and human lung tissue with and without the presence of Pc infection. For immunohistology, peroxidase-labelled rabbit antimouse immunoglobulin was used on paraffin sections (FIG. 2).

Screening of bacteriophage lambda gt11 clones was performed in *E. coli* strain Y1090 as described by Huynh et al. (Huynh, T. V. et al. In: *DNA Cloning: A Practical Approach* (D. M. Glover, ed.), Vol. 1, 1984, pp. 49–78), on HATF-137 nitrocellulose filters (Millipore, Bedford, Mass.) using alkaline phosphatase conjugated second antibody (BioRad Laboratories, Melville, N.Y.). A positive clone (FIG. 1) was purified through four rounds of rescreening. The purified clone, designated JFBIg10, was expressed as a fusion protein from lambda recombinant lysogens in *E. coli* Y1089 and screened on Western immunoblots against MAb6 with simultaneous negative controls (FIG. 3).

The DNA insert of the JFBIg10 clone was mapped by restriction endonuclease site analysis (FIG. 4). An EcoR1 fragment of the JFBIg10 DNA was subcloned into pUC18 for double-stranded dideoxy sequencing. Both strands were sequenced using a combination of primer walk strategy and Exo/Mung deletion strategy with commercial (New England Biolabs, Beverly, Mass.) and synthetic oligonucleotide primers. The entire 2814 bp sequence was checked by using PCR primers derived from the nucleotide sequence (Seq. ID #1) to amplify segments of the cloned DNA which were subsequently sequenced. Sequence information was assembled using sequence analysis software of the Genetics Computer Group, University of Wisconsin.

The JFBIg10 DNA insert was subcloned into pGEM3Z (Promega, Madison, Wis.) to make RNA probes. Sense and antisense $^{35}$S-labelled RNA sheared Riboprobes were synthesized by Lofstrand Labs Ltd. (Gaithersberg, Md.) from the T7 and Sp6 promoters of pGEM3Z. The JFBIg10 derived riboprobes were used in in situ hybridization to lung tissues from infected rats and from uninfected rats maintained on dexamethasone, low protein diet, and on trimethoprim-sulfamethoxazole to prevent the emergence of PCP. In situ hybridization was performed according to the method of Phelps and Floros, which is herein incorporated by reference. (Phelps, D. S. and Floros, J. (1988) *Am. Rev. Respir. Dis.* 137:939–942) Freshly collected lungs were cut into 2 mm sections and fixed in 4% paraformaldehyde in PBS (pH 7.2) at 4° C. and frozen sections cut at 4 to 8 microns. Each sense and antisense probe was tested on 20 slides from each of two animals exposed for up to four weeks after coating with photographic emulsion. Hematoxylin-eosin and methenamine silver-stained paraffin sections were examined on each lung to confirm the presence or absence of Pc infection. Slides were evaluated by three observers. Confocal microscopy was performed to demonstrate the close association of autoradiographic silver grains with areas of Pc infection in infected tissues (FIG. 6).

The riboprobes were also used to probe Northern blots of total RNA from infected and uninfected rat lungs. Equal amounts of total RNA were loaded in each lane. Each animal was evaluated for the presence or absence of PCP using methenamine silver and hematoxylin-eosin stained sections as well as on impression smears stained with DiffQuik (Baxter Scientific Products, McGraw Park, Ill.).

The riboprobes were also used to probe Southern blots containing total DNA from human, rat, mink, *E. coli* 1090, *S. cerevisiae*, Drosophila, and bacteriophage lambda gt11 in equal amounts in each lane (FIG. 7).

The in situ hybridization, Northern, and Southern analyses demonstrate that JFBIg10 DNA is of Pc and not mammalian host origin.

Analysis of the nucleotide sequence of JFBIg10 DNA (Seq. ID #1) reveals a 2814 bp cDNA insert encoding an 1197 bp open reading frame in a single orientation with a poly-A tract in a terminal location. No significant homologies were detected by comparison of the nucleotide sequence or deduced peptide sequence with GenBank or Swissprot databases using either the BlastX protocol (NIH) or the Wisconsin Wordsearch protocols (GCG). The highest level of similarity observed is of a short segment of the nucleotide sequence to a *Dictyostelium discoideum* (slime mold) cDNA for the phosphodiesterase gene. Amino acid sequence similarity of 12 aa was detected to a short region of the gp160 precursor from Human Immunodeficiency Virus-1.

4. Comparison of Rat- and Human-derived Nucleotide Sequence

Concerns about the relatedness of the organisms derived from clinical (human) samples and from rat-derived Pc were addressed by PCR amplification of human sequences using primers derived from the JFBIg10 rat Pc sequence. Human Pc bronchoalveolar lavage samples are routinely collected as part of a diagnostic process for patients thought to be infected with Pc at the Massachusetts General Hospital. Left over Bronchoalveolar lavage (BAL) after diagnostic tests and serum samples from the same patients were stored as sources of PC from humans after a positive diagnosis was made in any of these situations. Frozen samples include patients with AIDS, immune suppressive therapies and underlying malignancies. DNA (genomic) was prepared from these samples using a standard proteinase K and ethanol precipitation. Specific frozen samples are rapidly thawed at 37° C. 2 ml of each sample is collected into a sterile tube which is then diluted to a final concentration of 0.5% SDS, incubated with zymolyase 100-T at 100 units/ml for 15 minutes at 37° C.; incubated with proteinase K at 100 mg/ml at 60° C. for 2 hours; double extracted with phenol, phenol:chloroform, and chloroform; and finally, precipitated three times with sodium acetate and ethanol. These samples are then resuspended in PBS for use in PCR studies.

PCR amplification was performed in a Perkin Elmer thermal cycler using 40 cycles of amplification (92° C.×15 sec.; 50° C.×2 min.; 74° C.×3 min.) and terminal extension (72° C.×10 min.). Amplified segments were subcloned using the TA-cloning system (Invitrogen, San Diego, Calif.) and dideoxy-sequenced using both PCR and universal primers (Sequenase, US Biochemical, Cleveland, Ohio).

Equivalents

Those skilled in the art will recognize, or be able to ascertain using no more than routine experimentation, many equivalents to the specific embodiments of the invention described herein. Such equivalents are intended to be encompassed by the following claims.

I claim:

1. Isolated DNA having a nucleotide sequence selected from the group consisting of:

a) the nucleotide sequence of FIG. 5 (Sequence ID NO:1);

b) the nucleotide sequence of nucleotides 1 to 1056 of FIG. 8 (Sequence ID NO:3);
c) the nucleotide sequence of FIG. 9 (Sequence ID NO:4);
d) nucleotide sequences which, through the degeneracy of the genetic code, encode the same peptide gene product as that encoded by the nucleotide sequence of FIG. 5 (SEQ ID NO:1);
e) nucleotide sequences which, through the degeneracy of the genetic code, encode the same peptide gene product as that encoded by the nucleotide sequence of FIG. 9 (SEQ ID NO:4).

2. Isolated DNA encoding the amino acid sequence of FIG. 5 (Sequence ID NO:2).

3. Isolated DNA of *Pneumocystis carinii* from rat selected from the group consisting of: isolated DNA encoding a protein having the amino acid sequence encoded by the DNA of FIG. 5 (Sequence ID NO:1) and isolated DNA encoding a protein having the amino acid sequence encoded by the DNA of FIG. 9 (Sequence ID NO:4), wherein said proteins share an antigenic epitope with the gp116 surface antigen of said *Pneumocystis carinii* and bind a monoclonal antibody directed against the 110–120 kDa, a major surface antigen of *Pneumocystis Carinii*, or bind a monoclonal antibody directed against the 40–50 kDa major surface antigen of *Pneumocystis carinii.*

4. Isolated RNA encoded by a nucleotide sequence selected from the group consisting of:

a) the nucleotide sequence of FIG. 5 (Sequence ID NO:1);

b) the nucleotide sequence of necleotides 1 to 1056 of FIG. 8 (Sequence ID NO:3);

c) the nucleotide sequence of FIG. 9 (Sequence ID NO:4);

d) nucleotide sequences which, through the degeneracy of the genetic code, encode the same peptide gene product as that encoded by the nucleotide sequence of FIG. 5 (SEQ ID NO:1);

e) nucleotide sequences which, through the degeneracy of the genetic code, encode the same peptide gene product as that encoded by the nucleotide sequence of FIG. 9 (SEQ ID NO:4).

5. An expression vector comprising DNA having a nucleotide sequence selected from the group consisting of:

a) the nucleotide sequence of FIG. 5 (Sequence ID NO:1);

b) the nucleotide sequence of necleotides 1 to 1056 of FIG. 8 (Sequence ID NO: 3); and c) the nucleotide sequence of FIG. 9 (Sequence ID NO:4).

* * * * *